(12) United States Patent
Clements et al.

(10) Patent No.: US 8,781,186 B2
(45) Date of Patent: Jul. 15, 2014

(54) SYSTEM AND METHOD FOR ABDOMINAL SURFACE MATCHING USING PSEUDO-FEATURES

(75) Inventors: Logan Clements, Nashville, TN (US); James Stefansic, Nashville, TN (US); Prashanth Dumpuri, Nashville, TN (US); Senhu Li, Nashville, TN (US)

(73) Assignee: Pathfinder Therapeutics, Inc., Nashville, TN (US)

( * ) Notice: Subject to any disclaimer, the term of this patent is extended or adjusted under 35 U.S.C. 154(b) by 212 days.

(21) Appl. No.: 13/101,164

(22) Filed: May 5, 2011

(65) Prior Publication Data

US 2011/0274324 A1 Nov. 10, 2011

Related U.S. Application Data

(63) Continuation of application No. PCT/US2011/000786, filed on May 4, 2011.

(60) Provisional application No. 61/331,252, filed on May 4, 2010.

(51) Int. Cl.
*G06K 9/00* (2006.01)

(52) U.S. Cl.
USPC ........... 382/128; 382/131; 382/132; 382/133; 382/154; 382/294

(58) Field of Classification Search
CPC ............... A61B 19/52; A61B 19/5244; A61B 2019/505; A61B 2019/5268; A61B 2019/5289; A61B 19/00; G06T 2207/10072; G06T 2207/30004; G06T 7/0028
USPC .................. 382/128, 154, 131, 132, 133, 294
See application file for complete search history.

(56) References Cited

U.S. PATENT DOCUMENTS

| 5,053,042 A | 10/1991 | Bidwell |
| 5,158,088 A | 10/1992 | Nelson et al. |
| 5,186,174 A | 2/1993 | Schlondorff et al. |
| 5,251,165 A | 10/1993 | James, III |
| 5,251,635 A | 10/1993 | Dumoulin et al. |

(Continued)

FOREIGN PATENT DOCUMENTS

| DE | 19725137 C2 | 1/1999 |
| DE | 19909816 A1 | 5/2000 |

(Continued)

OTHER PUBLICATIONS

Clements, et al, "Robust surface registration using salient anatomical features in image-guided liver surgery," Medical Imaging 2006: Visualization, Image-guided Procedures, and Display: Proc. of the SPIE (2006).*

(Continued)

*Primary Examiner* — Tom Y Lu

(57) ABSTRACT

A system and method for using pre-procedural images for registration for image-guided therapy (IGT), also referred to as image-guided intervention (IGI), in percutaneous surgical application. Pseudo-features and patient abdomen and organ surfaces are used for registration and to establish the relationship needed for guidance. Three-dimensional visualizations of the vasculature, tumor(s), and organs may be generated for enhanced guidance information. The invention facilitates extensive pre-procedural planning, thereby significantly reducing procedural times. It also minimizes the patient exposure to radiation.

25 Claims, 8 Drawing Sheets

(56) References Cited

U.S. PATENT DOCUMENTS

| | | |
|---|---|---|
| 5,265,610 A | 11/1993 | Darrow et al. |
| 5,348,011 A | 9/1994 | NessAiver |
| 5,377,678 A | 1/1995 | Dumoulin et al. |
| 5,381,782 A | 1/1995 | DeLaRama et al. |
| 5,391,199 A | 2/1995 | Ben-Haim |
| 5,483,691 A | 1/1996 | Heck et al. |
| 5,483,961 A | 1/1996 | Kelly et al. |
| 5,577,502 A | 11/1996 | Darrow et al. |
| 5,581,183 A | 12/1996 | Lindstedt et al. |
| 5,644,612 A | 7/1997 | Moorman et al. |
| 5,671,739 A | 9/1997 | Darrow et al. |
| 5,718,241 A | 2/1998 | Ben-Haim et al. |
| 5,730,129 A | 3/1998 | Darrow et al. |
| 5,740,808 A | 4/1998 | Panescu et al. |
| 5,765,561 A | 6/1998 | Chen et al. |
| 5,769,861 A | 6/1998 | Vilsmeier |
| 5,787,886 A | 8/1998 | Kelly et al. |
| 5,803,089 A | 9/1998 | Ferre et al. |
| 5,840,025 A | 11/1998 | Ben-Haim |
| 5,868,673 A | 2/1999 | Vesely |
| 5,978,696 A | 11/1999 | VomLehn et al. |
| 6,016,439 A | 1/2000 | Acker |
| 6,019,724 A | 2/2000 | Gronningsaeter et al. |
| 6,026,173 A | 2/2000 | Svenson et al. |
| 6,078,175 A | 6/2000 | Foo |
| 6,122,538 A | 9/2000 | Sliwa, Jr. et al. |
| 6,144,875 A | 11/2000 | Schweikard et al. |
| 6,167,296 A | 12/2000 | Shahidi |
| 6,173,201 B1 | 1/2001 | Front |
| 6,190,395 B1 | 2/2001 | Williams |
| 6,198,959 B1 | 3/2001 | Wang |
| 6,201,987 B1 | 3/2001 | Dumoulin |
| 6,226,543 B1 | 5/2001 | Gilboa et al. |
| 6,226,548 B1 | 5/2001 | Foley et al. |
| 6,233,476 B1 | 5/2001 | Strommer et al. |
| 6,235,038 B1 | 5/2001 | Hunter et al. |
| 6,236,875 B1 | 5/2001 | Bucholz et al. |
| 6,246,896 B1 | 6/2001 | Dumoulin et al. |
| 6,246,898 B1 | 6/2001 | Vesely et al. |
| 6,267,769 B1 | 7/2001 | Truwit |
| 6,275,560 B1 | 8/2001 | Blake et al. |
| 6,282,442 B1 | 8/2001 | DeStefano et al. |
| 6,285,902 B1 | 9/2001 | Kienzle et al. |
| 6,298,259 B1 | 10/2001 | Kucharczyk et al. |
| 6,314,310 B1 | 11/2001 | Ben-Haim et al. |
| 6,314,311 B1 | 11/2001 | Williams et al. |
| 6,314,312 B1 | 11/2001 | Wessels et al. |
| 6,317,616 B1 | 11/2001 | Glossop |
| 6,317,619 B1 | 11/2001 | Boernert |
| 6,330,356 B1 | 12/2001 | Sundareswaran et al. |
| 6,332,089 B1 | 12/2001 | Acker et al. |
| 6,332,891 B1 | 12/2001 | Himes |
| 6,335,623 B1 | 1/2002 | Damadian et al. |
| 6,340,363 B1 | 1/2002 | Bolger et al. |
| 6,347,240 B1 | 2/2002 | Foley et al. |
| 6,348,058 B1 | 2/2002 | Melkent et al. |
| 6,351,573 B1 | 2/2002 | Schneider |
| 6,351,659 B1 | 2/2002 | Vilsmeier |
| 6,361,759 B1 | 3/2002 | Frayne et al. |
| 6,362,821 B1 | 3/2002 | Gibson et al. |
| 6,368,331 B1 | 4/2002 | Front et al. |
| 6,369,571 B1 | 4/2002 | Damadian et al. |
| 6,379,302 B1 | 4/2002 | Kessman et al. |
| 6,381,485 B1 | 4/2002 | Hunter et al. |
| 6,402,762 B2 | 6/2002 | Hunter et al. |
| 6,421,551 B1 | 7/2002 | Kuth et al. |
| 6,424,856 B1 | 7/2002 | Vilsmeier et al. |
| 6,425,865 B1 | 7/2002 | Salcudeail et al. |
| 6,430,430 B1 | 8/2002 | Gosche |
| 6,434,415 B1 | 8/2002 | Foley et al. |
| 6,434,507 B1 | 8/2002 | Clayton et al. |
| 6,437,571 B1 | 8/2002 | Danby et al. |
| 6,442,417 B1 | 8/2002 | Shahidi et al. |
| 6,445,186 B1 | 9/2002 | Damadian et al. |
| 6,445,943 B1 | 9/2002 | Ferre et al. |
| 6,455,182 B1 | 9/2002 | Silver |
| 6,461,372 B1 | 10/2002 | Jensen et al. |
| 6,468,265 B1 | 10/2002 | Evans et al. |
| 6,469,508 B1 | 10/2002 | Damadian et al. |
| 6,470,066 B2 | 10/2002 | Takagi et al. |
| 6,470,207 B1 | 10/2002 | Simon et al. |
| 6,473,635 B1 | 10/2002 | Rasche |
| 6,477,400 B1 | 11/2002 | Barrick |
| 6,478,793 B1 | 11/2002 | Cosman et al. |
| 6,478,802 B2 | 11/2002 | Kienzle et al. |
| 6,483,948 B1 | 11/2002 | Spink et al. |
| 6,484,049 B1 | 11/2002 | Seeley et al. |
| 6,485,413 B1 | 11/2002 | Boppart et al. |
| D466,609 S | 12/2002 | Glossop |
| 6,490,467 B1 * | 12/2002 | Bucholz et al. ............... 600/407 |
| 6,490,475 B1 | 12/2002 | Seeley et al. |
| 6,490,477 B1 | 12/2002 | Zylka et al. |
| 6,491,699 B1 | 12/2002 | Henderson et al. |
| 6,491,702 B2 | 12/2002 | Heilbrun et al. |
| 6,493,574 B1 | 12/2002 | Ehnholm et al. |
| 6,496,007 B1 | 12/2002 | Damadian et al. |
| 6,501,981 B1 | 12/2002 | Schweikard et al. |
| 6,504,893 B1 | 1/2003 | Flohr et al. |
| 6,504,894 B2 | 1/2003 | Pan et al. |
| 6,514,259 B2 * | 2/2003 | Picard et al. .................... 606/88 |
| 6,517,485 B2 | 2/2003 | Torp et al. |
| 6,527,443 B1 | 3/2003 | Vilsmeier et al. |
| 6,535,756 B1 | 3/2003 | Simon et al. |
| 6,538,634 B1 | 3/2003 | Chui et al. |
| 6,539,127 B1 | 3/2003 | Roche et al. |
| 6,541,973 B1 | 4/2003 | Danby et al. |
| 6,544,041 B1 | 4/2003 | Damadian |
| 6,547,782 B1 | 4/2003 | Taylor |
| 6,558,333 B2 | 5/2003 | Gilboa et al. |
| 6,567,687 B2 | 5/2003 | Front et al. |
| 6,580,938 B1 | 6/2003 | Acker |
| 6,584,174 B2 | 6/2003 | Schubert et al. |
| 6,584,339 B2 | 6/2003 | Galloway, Jr. et al. |
| 6,591,130 B2 | 7/2003 | Shahidi |
| 6,606,513 B2 | 8/2003 | Lardo et al. |
| 6,609,022 B2 | 8/2003 | Vilsmeier et al. |
| 6,636,757 B1 | 10/2003 | Jascob et al. |
| 6,650,924 B2 | 11/2003 | Kuth et al. |
| 6,666,579 B2 | 12/2003 | Jensen |
| 6,674,833 B2 | 1/2004 | Shahidi et al. |
| 6,675,032 B2 | 1/2004 | Chen et al. |
| 6,675,033 B1 | 1/2004 | Lardo et al. |
| 6,687,531 B1 | 2/2004 | Ferre et al. |
| 6,690,960 B2 | 2/2004 | Chen et al. |
| 6,694,167 B1 | 2/2004 | Ferre et al. |
| 6,697,664 B2 | 2/2004 | Kienzle, III et al. |
| 6,711,429 B1 | 3/2004 | Gilboa et al. |
| 6,714,629 B2 | 3/2004 | Vilsmeier |
| 6,714,810 B2 | 3/2004 | Grzeszczuk et al. |
| 6,725,080 B2 | 4/2004 | Melkent et al. |
| 6,738,656 B1 | 5/2004 | Ferre et al. |
| 6,772,002 B2 | 8/2004 | Schmidt et al. |
| 6,774,624 B2 | 8/2004 | Anderson et al. |
| 6,782,287 B2 * | 8/2004 | Grzeszczuk et al. .......... 600/424 |
| 6,785,571 B2 | 8/2004 | Glossop |
| 6,796,988 B2 | 9/2004 | Melkent et al. |
| 6,823,207 B1 | 11/2004 | Jensen et al. |
| 6,826,423 B1 | 11/2004 | Hardy et al. |
| 6,837,892 B2 * | 1/2005 | Shoham ....................... 606/130 |
| 6,850,794 B2 | 2/2005 | Shahidi |
| 6,856,826 B2 | 2/2005 | Seeley et al. |
| 6,856,827 B2 | 2/2005 | Seeley et al. |
| 6,892,090 B2 | 5/2005 | Verard et al. |
| 6,898,303 B2 | 5/2005 | Armato, III et al. |
| 6,907,281 B2 | 6/2005 | Grzeszczuk |
| 6,920,347 B2 | 7/2005 | Simon et al. |
| 6,932,823 B2 | 8/2005 | Grimm et al. |
| 6,934,575 B2 | 8/2005 | Ferre et al. |
| 6,968,224 B2 | 11/2005 | Kessman et al. |
| 6,978,166 B2 | 12/2005 | Foley et al. |
| 7,015,859 B2 | 3/2006 | Anderson |
| 7,043,961 B2 | 5/2006 | Pandey et al. |
| 7,050,845 B2 | 5/2006 | Vilsmeier |
| 7,072,707 B2 | 7/2006 | Galloway, Jr. et al. |

(56) References Cited

U.S. PATENT DOCUMENTS

| | | | |
|---|---|---|---|
| 7,103,399 B2* | 9/2006 | Miga et al. ............... | 600/425 |
| 7,139,601 B2 | 11/2006 | Bucholz et al. | |
| 7,153,297 B2 | 12/2006 | Peterson | |
| 7,171,257 B2 | 1/2007 | Thomson | |
| 7,174,201 B2 | 2/2007 | Govari et al. | |
| 7,260,426 B2 | 8/2007 | Schweikard et al. | |
| 7,280,710 B1* | 10/2007 | Castro-Pareja et al. ....... | 382/303 |
| 7,327,865 B2 | 2/2008 | Fu et al. | |
| 7,389,116 B1* | 6/2008 | Patro ............................ | 455/466 |
| 7,398,116 B2 | 7/2008 | Edwards | |
| 7,505,037 B2 | 3/2009 | Wang | |
| 7,519,209 B2 | 4/2009 | Dawant et al. | |
| 7,620,226 B2 | 11/2009 | Unal et al. | |
| 7,689,021 B2 | 3/2010 | Shekhar et al. | |
| 7,715,604 B2* | 5/2010 | Sun et al. ...................... | 382/128 |
| 7,835,778 B2* | 11/2010 | Foley et al. ................... | 600/407 |
| 7,853,307 B2 | 12/2010 | Edwards | |
| 7,860,000 B2 | 12/2010 | Wigard et al. | |
| 7,884,754 B1 | 2/2011 | Alouani et al. | |
| 8,010,180 B2* | 8/2011 | Quaid et al. .................. | 600/424 |
| 8,358,818 B2 | 1/2013 | Miga et al. | |
| 2001/0007918 A1 | 7/2001 | Vilsmeier et al. | |
| 2001/0025142 A1 | 9/2001 | Wessels et al. | |
| 2001/0029333 A1 | 10/2001 | Shahidi | |
| 2001/0031919 A1 | 10/2001 | Strommer et al. | |
| 2001/0031985 A1 | 10/2001 | Gilboa et al. | |
| 2001/0036245 A1 | 11/2001 | Kienzle et al. | |
| 2001/0041835 A1 | 11/2001 | Front et al. | |
| 2002/0035321 A1 | 3/2002 | Bucholz et al. | |
| 2002/0044631 A1 | 4/2002 | Graumann et al. | |
| 2002/0049375 A1 | 4/2002 | Strommer et al. | |
| 2002/0049378 A1 | 4/2002 | Grzeszczuk et al. | |
| 2002/0075994 A1 | 6/2002 | Shahidi et al. | |
| 2002/0077543 A1 | 6/2002 | Grzeszczuk | |
| 2002/0077544 A1 | 6/2002 | Shahidi | |
| 2002/0082492 A1 | 6/2002 | Grzeszczuk | |
| 2002/0085681 A1 | 7/2002 | Jensen | |
| 2002/0095081 A1 | 7/2002 | Vilsmeier | |
| 2002/0143317 A1 | 10/2002 | Glossop | |
| 2002/0161295 A1 | 10/2002 | Edwards et al. | |
| 2003/0000535 A1 | 1/2003 | Galloway, Jr. et al. | |
| 2003/0004411 A1 | 1/2003 | Govari et al. | |
| 2003/0016852 A1 | 1/2003 | Kaufman et al. | |
| 2003/0018251 A1 | 1/2003 | Solomon | |
| 2003/0023161 A1 | 1/2003 | Govari et al. | |
| 2003/0028091 A1 | 2/2003 | Simon et al. | |
| 2003/0029464 A1 | 2/2003 | Chen et al. | |
| 2003/0032878 A1 | 2/2003 | Shahidi | |
| 2003/0040667 A1 | 2/2003 | Feussner et al. | |
| 2003/0074011 A1 | 4/2003 | Gilboa et al. | |
| 2003/0088179 A1 | 5/2003 | Seeley et al. | |
| 2003/0125622 A1 | 7/2003 | Schweikard et al. | |
| 2003/0130576 A1 | 7/2003 | Seeley et al. | |
| 2003/0139663 A1 | 7/2003 | Graumann | |
| 2003/0208116 A1 | 11/2003 | Liang et al. | |
| 2003/0208122 A1 | 11/2003 | Melkent et al. | |
| 2003/0216631 A1 | 11/2003 | Bloch et al. | |
| 2003/0220557 A1 | 11/2003 | Cleary et al. | |
| 2004/0006268 A1 | 1/2004 | Gilboa et al. | |
| 2004/0009459 A1 | 1/2004 | Anderson et al. | |
| 2004/0019263 A1 | 1/2004 | Jutras et al. | |
| 2004/0034300 A1 | 2/2004 | Verard et al. | |
| 2004/0049121 A1 | 3/2004 | Yaron | |
| 2004/0059217 A1 | 3/2004 | Kessman et al. | |
| 2004/0076259 A1 | 4/2004 | Jensen et al. | |
| 2004/0092815 A1 | 5/2004 | Schweikard et al. | |
| 2004/0097805 A1 | 5/2004 | Verard et al. | |
| 2004/0097806 A1 | 5/2004 | Hunter et al. | |
| 2004/0116803 A1 | 6/2004 | Jascob et al. | |
| 2004/0122311 A1 | 6/2004 | Cosman | |
| 2004/0138548 A1 | 7/2004 | Strommer et al. | |
| 2004/0152970 A1 | 8/2004 | Hunter et al. | |
| 2004/0152974 A1 | 8/2004 | Solomon | |
| 2004/0153062 A1 | 8/2004 | McGinley et al. | |
| 2004/0193042 A1 | 9/2004 | Scampini et al. | |
| 2004/0210125 A1 | 10/2004 | Chen et al. |
| 2004/0267242 A1 | 12/2004 | Grimm et al. |
| 2005/0010099 A1 | 1/2005 | Raabe et al. |
| 2005/0027186 A1 | 2/2005 | Chen et al. |
| 2005/0033149 A1 | 2/2005 | Strommer et al. |
| 2005/0065433 A1 | 3/2005 | Anderson |
| 2005/0085793 A1 | 4/2005 | Glossop |
| 2005/0101855 A1 | 5/2005 | Miga et al. |
| 2005/0107688 A1 | 5/2005 | Strommer |
| 2005/0113809 A1 | 5/2005 | Melkent et al. |
| 2005/0143651 A1 | 6/2005 | Verard et al. |
| 2005/0169510 A1 | 8/2005 | Zuhars et al. |
| 2005/0182319 A1 | 8/2005 | Glossop |
| 2005/0197568 A1 | 9/2005 | Vass et al. |
| 2005/0203383 A1 | 9/2005 | Moctezuma de la Barrera et al. |
| 2005/0234335 A1 | 10/2005 | Simon et al. |
| 2005/0288574 A1 | 12/2005 | Thornton et al. |
| 2005/0288578 A1 | 12/2005 | Durlak |
| 2006/0004281 A1 | 1/2006 | Saracen |
| 2006/0025677 A1 | 2/2006 | Verard et al. |
| 2006/0045318 A1 | 3/2006 | Schoisswohl et al. |
| 2006/0050942 A1 | 3/2006 | Bertram et al. |
| 2006/0050988 A1 | 3/2006 | Kraus et al. |
| 2006/0058647 A1 | 3/2006 | Strommer et al. |
| 2006/0063998 A1 | 3/2006 | von Jako et al. |
| 2006/0064006 A1 | 3/2006 | Strommer et al. |
| 2006/0074292 A1 | 4/2006 | Thomson et al. |
| 2006/0074299 A1 | 4/2006 | Sayeh |
| 2006/0074304 A1 | 4/2006 | Sayeh |
| 2006/0079759 A1 | 4/2006 | Vaillant et al. |
| 2006/0084867 A1 | 4/2006 | Tremblay et al. |
| 2006/0093089 A1 | 5/2006 | Vertatschitsch et al. |
| 2006/0094958 A1 | 5/2006 | Marquart et al. |
| 2006/0106292 A1 | 5/2006 | Anderson |
| 2006/0116634 A1 | 6/2006 | Shachar |
| 2006/0122497 A1 | 6/2006 | Glossop |
| 2006/0173269 A1 | 8/2006 | Glossop |
| 2006/0173291 A1 | 8/2006 | Glossop |
| 2006/0189867 A1 | 8/2006 | Revie et al. |
| 2006/0247511 A1 | 11/2006 | Anderson |
| 2006/0258938 A1 | 11/2006 | Hoffman et al. |
| 2007/0032723 A1 | 2/2007 | Glossop |
| 2007/0038058 A1 | 2/2007 | West et al. |
| 2007/0066887 A1 | 3/2007 | Mire et al. |
| 2007/0086659 A1 | 4/2007 | Chefd'hotel et al. |
| 2007/0110289 A1 | 5/2007 | Fu et al. |
| 2007/0129629 A1 | 6/2007 | Beauregard et al. |
| 2007/0167699 A1 | 7/2007 | Lathuiliere et al. |
| 2007/0167744 A1 | 7/2007 | Beauregard et al. |
| 2008/0045972 A1 | 2/2008 | Wagner et al. |
| 2008/0071215 A1 | 3/2008 | Woods et al. |
| 2008/0123927 A1 | 5/2008 | Miga et al. |
| 2008/0193006 A1 | 8/2008 | Udupa et al. |
| 2008/0279430 A1 | 11/2008 | Chan et al. |
| 2009/0177081 A1 | 7/2009 | Joskowicz et al. |
| 2009/0240237 A1 | 9/2009 | Goldfarb et al. |
| 2010/0030232 A1 | 2/2010 | Zehavi et al. |
| 2010/0036245 A1 | 2/2010 | Yu et al. |
| 2010/0042046 A1 | 2/2010 | Chang et al. |
| 2010/0210938 A1 | 8/2010 | Verard et al. |
| 2012/0082356 A1 | 4/2012 | Zankowski |
| 2012/0330635 A1 | 12/2012 | Miga et al. |
| 2013/0030286 A1 | 1/2013 | Alouani et al. |
| 2013/0044930 A1 | 2/2013 | Li et al. |
| 2013/0178745 A1 | 7/2013 | Kyle et al. |

FOREIGN PATENT DOCUMENTS

| | | |
|---|---|---|
| DE | 10161160 | 6/2003 |
| DE | 10136709 B4 | 9/2004 |
| DE | 102005010010 | 9/2005 |
| DE | 19829224 B4 | 12/2005 |
| DE | 102004030836 | 1/2006 |
| DE | 10000937 B4 | 2/2006 |
| DE | 102005038394 | 3/2006 |
| DE | 102005050286 | 4/2006 |
| DE | 102004058122 | 7/2006 |
| EP | 0501993 | 6/1997 |
| EP | 0977510 | 2/2000 |

(56) References Cited

FOREIGN PATENT DOCUMENTS

| | | |
|---|---|---|
| EP | 1079240 | 2/2001 |
| EP | 1181897 | 2/2002 |
| EP | 0869745 | 11/2002 |
| EP | 1319368 | 6/2003 |
| EP | 1374792 | 1/2004 |
| EP | 1374793 | 1/2004 |
| EP | 1391181 | 2/2004 |
| EP | 1421913 | 5/2004 |
| EP | 1504726 | 2/2005 |
| EP | 1152706 | 3/2005 |
| EP | 1519140 | 3/2005 |
| EP | 1523951 | 4/2005 |
| EP | 1464285 | 6/2005 |
| EP | 0900048 | 8/2005 |
| EP | 1561423 | 8/2005 |
| EP | 1629774 | 3/2006 |
| EP | 1629789 | 3/2006 |
| EP | 1504713 | 7/2008 |
| FR | 2876273 | 4/2006 |
| JP | 2001-276080 | 10/2001 |
| JP | 2003-220061 | 8/2003 |
| WO | WO 95/01757 | 1/1995 |
| WO | WO 96/08209 A2 | 3/1996 |
| WO | WO 96/08209 A3 | 3/1996 |
| WO | WO 96/10949 | 4/1996 |
| WO | WO 97/29699 | 8/1997 |
| WO | WO 97/29709 | 8/1997 |
| WO | WO 98/36684 | 8/1998 |
| WO | WO 99/16352 | 4/1999 |
| WO | WO 99/43253 | 9/1999 |
| WO | WO 00/16684 | 3/2000 |
| WO | WO 00/28911 | 5/2000 |
| WO | WO 00/47103 | 8/2000 |
| WO | WO 00/49958 | 8/2000 |
| WO | WO 00/57767 | 10/2000 |
| WO | WO 00/69335 | 11/2000 |
| WO | WO 01/01845 | 1/2001 |
| WO | WO 01/37748 | 5/2001 |
| WO | WO 01/62134 | 8/2001 |
| WO | WO 01/64124 | 9/2001 |
| WO | WO 01/76496 | 10/2001 |
| WO | WO 01/76497 | 10/2001 |
| WO | WO 01/87136 | 11/2001 |
| WO | WO 01/93745 | 12/2001 |
| WO | WO 02/00093 | 1/2002 |
| WO | WO 02/00103 | 1/2002 |
| WO | WO 02/19936 | 3/2002 |
| WO | WO 02/22015 | 3/2002 |
| WO | WO 02/24051 | 3/2002 |
| WO | WO 02/056770 | 7/2002 |
| WO | WO 02/064011 | 8/2002 |
| WO | WO 02/082375 | 10/2002 |
| WO | WO 02/098273 | 12/2002 |
| WO | WO 2004/019799 | 3/2004 |
| WO | WO 2004/046754 | 6/2004 |
| WO | WO 2004/060157 | 7/2004 |
| WO | WO 2004/062497 | 7/2004 |
| WO | WO 2005/070318 | 8/2005 |
| WO | WO 2005/077293 | 8/2005 |
| WO | WO 2005/101277 | 10/2005 |
| WO | WO 2005/111942 | 11/2005 |
| WO | WO 2006/002396 | 1/2006 |
| WO | WO 2006/005021 | 1/2006 |
| WO | WO 2006/027781 | 3/2006 |
| WO | WO 2006/039009 | 4/2006 |
| WO | WO 2006/051523 | 5/2006 |
| WO | WO 2006/090141 | 8/2006 |
| WO | WO 2007/002079 | 1/2007 |
| WO | WO 2007/031314 | 3/2007 |
| WO | WO 2007/062051 | 5/2007 |
| WO | WO 2007/084893 | 7/2007 |
| WO | WO 2012/145367 | 10/2012 |
| WO | WO 2012/169990 | 12/2012 |
| WO | WO 2013/016251 | 1/2013 |

OTHER PUBLICATIONS

Clements, et al, "Robust surface registration using salient anatomical features for image-guided liver surgery: Algorithm and validation," Medical Physics, vol. 35, No. 6, pp. 2528-2540 (2008).*
International Search Report and Written Opinion for International Application No. PCT/US2011/000786, mailed Jan. 21, 2013.
Office Action for U.S. Appl. No. 13/449,805, mailed Nov. 20, 2013.
International Search Report and Written Opinion for International Application No. PCT/US2012/034030, mailed Nov. 30, 2012.
Office Action for U.S. Appl. No. 13/555,144, mailed Oct. 25, 2013.
International Search Report for International Application No. PCT/US2012/047775, mailed Feb. 1, 2013.
Office Action for U.S. Appl. No. 13/624,221, mailed Oct. 8, 2013.
International Search Report for International Application No. PCT/US2012/056594, mailed Mar. 4, 2013.
International Search Report for International Application No. PCT/US2012/056586, mailed Feb. 26, 2013.
Ahn, S. J. et al., "Orthogonal distance fitting of implicit curves and surfaces," IEEE Transactions on Pattern Analysis and Machine Intelligence, vol. 24, No. 5, pp. 620-638, 2002.
Alouani, A. T. et al., Theory of distributed estimation using multiple asynchronous sensors, IEEE Transactions on Aerospace and Electronic Systems, vol. 41, No. 2, pp. 717-722, Apr. 2005.
American Cancer Society, "Cancer Facts and Figures," American Cancer Society, Atlanta, 2004, 60 pages.
Antipolis, S., "Project-team epidaure: Epidaure, project images, diagnostic, automatique, robotique," Activity Report, INRIA, 2004, 50 pages.
Arun, K. S. et al., "Least-squares fitting of two 3-D point sets," IEEE Transactions on Pattern Analysis and Machine Intelligence, vol. 9, No. 5, pp. 698-700, 1987.
Ayache, N., "Epidaure: A research project in medical image analysis, simulation, and robotics at INRIA," IEEE Transactions on Medical Imaging, vol. 22, pp. 1185-1201, 2003.
Balay, S. et al., "Efficient Management of Parallelism in Object-Oriented Numerical Software Libraries," Cambridge, MA: Birkhauser, pp. 163-202, 1997.
Bao, P. et al., "Ultrasound-to-computer-tomography registration for image-guided laparoscopic liver surgery," Surg. Endosc., pp. 424-429, vol. 19, Electronic Publication, 2005.
Barnes, S. L. et al., "A novel model-gel-tissue assay analysis for comparing tumor elastic properties to collagen content," Biomech Model Mechanobiol., vol. 8, pp. 337-343, 2009.
Barnes, S. L. et al., "Development of a mechanical testing assay for fibrotic murine liver," Medical Physics, vol. 34, No. 11, pp. 4439-4450, 2007.
Barnes, S. L. et al., "Development of a mechanical testing assay for modulus analysis of fibrotic murine liver," 6th International Conference on the Ultrasonic Measurement and Imaging of Tissue Elasticity, Santa Fe, New Mexico, p. 48, Nov. 2007.
Bentley, J. L. "Multidimensional binary search trees used for associative searching," Communications of the ACM, vol. 18, No. 9, pp. 509-517, 1975.
Besl, P. J. et al., "A Method for Registration of 3-D Shapes," IEEE Transactions on Pattern Analysis and Machine Intelligence, vol. 14, No. 2, pp. 239-256, 1992.
Blackall, J. M. et al., "A statistical model of respiratory motion and deformation of the liver," Medical Image Computing and Computer-Assisted Interventions, S. Verlag, Ed. Berlin, 2208, pp. 1338-1340, 2001.
Blumgart, L. H. et al., "Surgical options in the treatment of hepatic metastases from colorectal cancer," In Current Problems in Surgery, vol. 32, No. 5, pp. 335-421, 1995.
Bradley, A. L. et al, "Surgical experience with hepatic colorectal metastasis," The American Surgeon, vol. 65, pp. 560-567, 1999.
Cao, Z., "Segmentation of medical images using level set-based methods," Pro Quest Dissertations and Theses, Electrical Engineering, Computer Engineering, and Computer Science Nashville: Vanderbilt University, 2004, 15 pages.

(56) References Cited

OTHER PUBLICATIONS

Carr, J. et al., "Smooth surface reconstruction from noisy range data," ACM Graphite 2003, Melbourne, Australia, pp. 119-126, 2003.

Carter, F. J. et al., "Measurements and modelling of the compliance of human and porcine organs," Medical Image Analysis, vol. 5, pp. 231-236, Dec. 2001.

Cash, D. M. et al., "Compensating for intraoperative soft-tissue deformations using incomplete surface data and finite elements," IEEE Transactions on Medical Imaging, vol. 24. No. 11, pp. 1479-1491, 2005.

Cash, D. M. et al., "Concepts and preliminary data toward the realization of image-guided liver surgery," J. Gastrointest. Surg., vol. 11, pp. 844-859, 2007.

Cash, D. M. et al., "Fast, accurate surface acquisition using a laser range scanner for image-guided liver surgery," Medical Imaging 2002: Visualization, display, and image-guided procedures: Proc. of the SPIE 2002, vol. 4681, pp. 100-110, 2002.

Cash, D. M. et al., "Incorporation of a laser range scanner into image-guided liver surgery: Surface acquisition, registration, and tracking," Medical Physics, vol. 30, No. 7, pp. 1671-1682, Jul. 2003.

Chui, H. et al., "A new point matching algorithm for non-rigid registration," Computer Vision and Image Understanding, vol. 89, pp. 114-141, 2003.

Clements, L. W. et al., "Robust surface registration using salient anatomical features in image-guided liver surgery," Proc. of SPIE: Medical Imaging 2006, vol. 6141, Feb. 11-16, 2006.

Clements, L. W. et al., "Atlas-based method for model updating in image-guided liver surgery," SPIE Medical Imaging 2007: Visualization, Image Guided Procedures, and Modeling, San Diego, CA. (12 pages).

Clements, L. W. et al., "Organ surface deformation measurement and analysis in open hepatic surgery: Method and preliminary results from 12 clinical cases," IEEE Transactions on Biomedical Engineering, vol. 58, No. 8, pp. 2280-2289, 2011.

Clements, L. W. et al., "Salient anatomical features for robust surface registration and atlas-based model updating image-guided liver surgery," Ph.D. Dissertation, Vanderbilt University, Department of Biomedical Engineering, May 2009, 171 pages.

Cohnert, T. U. et al., "Preoperative risk assessment of hepatic resection for malignant disease," World Journal of Surgery, vol. 21, No. 4, pp. 396-400, 1997.

Davatzikos, C. et al., "A framework for predictive modeling of anatomical deformations," IEEE Transactions on Medical Imaging, vol. 20, No. 8, pp. 836-843, 2001.

Davatzikos, C. et al., "Convexity analysis of active contour problems," Image and Vision Computing, vol. 17, pp. 27-36, 1999.

Davatzikos, C., "Measuring biological shape using geometry-based shape transformations," Image and Vision Computing, vol. 19, pp. 63-74, 2001.

Dawant, B. M. et al., "Robust segmentation of medical images using geometric deformable models and a dynamic speed function," Medical Image Computing and Computer-Assisted Intervention 2001. vol. 2208, N. A. Viergever, (ed.), Springer Verlag, 2001.

Dematteo, R. P. et al., "Anatomic segmental hepatic resection is superior to wedge resection as an oncologic operation for colorectal liver metastates," J. Gastrointest. Surg., vol. 4, No. 2, pp. 178-184, 2000.

Dumpuri, P. et al., "Comparison of pre/post-operative CT image volumes to preoperative digitization of partial hepatectomies: A feasibility study in surgical validation," SPIE Medical Imaging 2009: Visualization, Image-Guided Procedures and Modeling Conference, 7 pages.

Dumpuri, P. et al., "An atlas-based method to compensate for brain shift: Preliminary results," Medical Image Analysis, vol. 11, pp. 128-145, 2007.

Dumpuri, P. et al., "Automated brain shift correction using a precomputed deformation atlas," Proc. of SPIE: Medical Imaging 2006, vol. 6141, Feb. 11-16, 2006.

Dumpuri, P. et al., "Model-updated image-guided liver surgery: preliminary results using intraoperative surface characterization," SPIE 2010: Medical Imaging Visualization, Image-Guided Procedures, and Modeling Conference, 7 pages.

Dumpuri, P. et al., "Model-updated image guidance: A statistical approach to gravity-induced brain shift," in Medical Image Computing and Computer-Assisted Intervention-Miccai 2003, Pt 1. vol. 2878 Berlin: Springer-Verlag Berlin, 2003, pp. 375-382.

Fitzpatrick, J. M. et al., "Predicting error in rigid-body, point-based registration," IEEE Transactions on Medical Imaging, vol. 17, No. 5, pp. 694-702, Oct. 1998.

Frericks, B. B. et al., "3D CT modeling of hepatic vessel architecture and volume calculation in living donated liver transplantation," Eur Radiol, vol. 14, pp. 326-333, 2004.

Garden, O. J. et al., "Anatomy of the liver," Hepatobiliary and Pancreatic Surgery, Fifth Edition, S. D. Carter et al., Eds. London: Chapman and Hall Medical, 1996, pp. 1-4.

Godin, G. et al., "A method for the registration of attributed range images," Proc. 3DIM 2001, May 2001, pp. 179-186.

Hackworth, D. et al., "A dual compute resource strategy for computational model assisted therapeutic interventions," SPIE Medical Imaging 2009: Visualization, Image-Guided Procedures, and Modeling, vol. 7261, pp. 72612R1-72612R-8, 2009.

Hartkens, T. et al., "Measurement and analysis of brain deformation during neurosurgery," IEEE Transactions on Medical Imaging, vol. 22, No. 1, pp. 82-92, Jan. 2003.

Herline, A. J. et al., "Image-guided surgery: Preliminary feasibility studies of frameless stereotactic liver surgery," Arch. Surg., vol. 134, pp. 644-650, 1999.

Herline, A. J. et al., "Surface registration for use in interactive, image-guided liver surgery," Springer-Verlag Berlin Heidelberg, pp. 892-899, 1999.

Hermoye, L. et al., "Liver segmentation in living liver transplant donors: Comparison of semiautomatic and manual methods," Radiology, vol. 234, pp. 171-178, Jan. 2005.

Jarnagin, W. R. et al., "Improvement in perioperative outcome after hepatic resection: Analysis of 1,803 consecutive cases over the past decade," Ann. Surg., vol. 236, No. 4, pp. 397-407, 2002.

Johnson, A. E. et al., "Registration and integration of textured 3D data," Image and Vision Computing, vol. 17, No. 2, pp. 135-147, 1999.

Julier, S. J. et al., "Unscented Filtering and Nonlinear Estimation," Proceedings of the IEEE, vol. 92, No. 3, pp. 401-422, 2004.

Knaus, D. et al., "System for laparoscopic tissue tracking," IEEE International Symposium on Biomedical Imaging, Washington, D.C., 2006, 4 pages.

Kyriacou, S. K. et al., "A biomechanical model of soft tissue deformation, with applications to non-rigid registration of brain images with tumor pathology," Medical Image Computing and Computer-Assisted Intervention-Miccai '98, vol. 1496, pp. 531-538, 1998.

Kyriacou, S. K. et al., "A framework for predictive modeling of intra-operative deformations: a simulation-based study," Medical Image Computing and Computer-Assisted Intervention-Miccai, vol. 1935, pp. 634-642, 2000.

Lang, H. et al., "Extended left hepatectomy-modified operation planning based on three-dimensional visualization and liver anatomy," Langenbecks Arch Surg., vol. 389, pp. 306-310, 2004.

Laurent, C. et al., "Influence of postoperative morbidity on long-term survival following liver resection for colorectal metastases," British Journal of Surgery, vol. 90, pp. 1131-1136, 2003.

Lefebvre, T. et al., "Kalman filters for non-linear systems: a comparison of performance," Int. J. Control, vol. 77, No. 7, pp. 639-653, May 2004.

Lorensen, W. E. et al., "Marching cubes: A high resolution 3D surface construction algorithm," ACM Computer Graphics, vol. 21, No. 4, pp. 163-169, 1987.

Malladi, R. et al., "Shape modeling with front propagation: A level set approach," IEEE Transactions on Pattern Analysis and Machine Intelligence, vol. 17, No. 2, pp. 158-175, 1995.

Masutani, Y. et al., "Modally controlled free form deformation for non-rigid registration in image-guided liver surgery," Medical Image Computing and Computer-Assisted Interventions, Springer-Verlag Berlin Heidelberg, vol. 2208, pp. 1275-1278, 2001.

(56) References Cited

OTHER PUBLICATIONS

Maurer, Jr., C. R. et al., "Registration of 3-D images using weighted geometrical features," IEEE Transactions on Medical Imaging, vol. 15, No. 6, pp. 836-849, 1996.

Miga, M. I., "The changing roles for soft-tissue modeling: Therapy guidance," Workshop on Clinical Image-Guided Therapy: Opportunities and Needs, Sponsored by the National Institutes of Health and National Center for Image-Guided Therapy, Washington D.C., Mar. 2008, 1 page.

Miga, M. I. et al., "Incorporation of surface-based deformations for updating images intraoperatively," Visualization, Display, and Image-Guided Procedures, Proceedings of SPIE, vol. 4319, pp. 169-178, 2001.

Miga, M. I. et al., "Intraoperative registration of the liver for image-guided surgery using laser range scanning and deformable models," Medical Imaging 2003: Visualization, Image-guided Procedures, and Display, San Diego, 2003, pp. 350-359.

Nabavi, A. et al., "Serial intraoperative magnetic resonance imaging of brain shift," Neurosurgery, vol. 48, No. 4, pp. 787-798, 2001.

Nabavi, A. et al., "Image-guided therapy and intraoperative MRI in neurosurgery," Minimally Invasive Therapy & Allied Technologies, vol. 9(3/4), pp. 277-286, 2000.

Nimsky, C. et al., "Intraoperative magnetic resonance tomography. Experiences in neurosurgery," Nervenarzt, vol. 71, No. 12, pp. 987-994, 2000.

Nimsky, C. et al., "Quantification of, visualization of, and compensation for brain shift using intraoperative magnetic resonance imaging," Neurosurgery, vol. 47, No. 5, pp. 1070-1079, 2000.

Penney, G. P. et al., "Registration of freehand 3D ultrasound and magnetic resonance liver images," Medical Image Analysis, vol. 8, pp. 81-91, 2004.

Platenik, L. A. et al., "In vivo quantification of retraction deformation modeling for updated image-guidance during neurosurgery," IEEE Transactions on Biomedical Engineering, vol. 49, No. 8, pp. 823-835, Aug. 2002.

Pluim, J. P. W. et al., "Image registration by maximization of combined mutual information and gradient information," IEEE Transactions on Medical Imaging, vol. 19, No. 8, pp. 809-814, 2000.

Saad, Y. et al., "GMRES: A generalized minimal residual algorithm for solving nonsymmetric linear systems," SIAM J. Sci. Statist. Comput., vol. 7, No. 3, pp. 856-869, 1986.

Scheele, J. et al., "Resection of colorectal liver metastasis," World Journal of Surgery, vol. 19, pp. 59-71, 1995.

Schindl, M. J. et al., "The value of residual liver volume as a predictor of hepatic dysfunction and infection after major liver resection," Gut, vol. 54, pp. 289-296, 2005.

Selle, D. et al., "Analysis of vasculature of liver surgical planning," IEEE Transactions on Medical Imaging, vol. 21, No. 11, pp. 1344-1257, 2002.

Sgouros, S. et al., "The clinical value of electroencephalogram/magnetic resonance imaging co-registration and three-dimensional reconstruction in the surgical treatment of epileptogenic lesions," Child's Nervous System, vol. 17, pp. 139-144, 2001.

Sharp, G. C. et al., "ICP registration using invariant features," IEEE Transactions on Pattern Analysis and Machine Intelligence, vol. 24, No. 1, pp. 90-102, Jan. 2002.

Sheiner, P. A. et al., "Treatment of metastatic cancer to the liver," Seminars in Liver Disease, vol. 14, No. 2, pp. 169-177, 1994.

Stevanovic, M. et al., "Modeling contact between rigid sphere and elastic layer bonded to rigid substrate," IEEE Transactions on Components and Packaging Technologies, vol. 24, No. 2, pp. 207-212, 2001.

Stone, M. D. et al., "Surgical therapy for recurrent liver metastases from colorectal cancer," Arch Surg, vol. 125, pp. 718-722, 1990.

Suthau, T. et al., "A concept work for augmented reality visualization based on a medical application in liver surgery," Proc. of the ISPRS Commission V Symposium, Corfu, Greece, 2002, pp. 274-280.

Yamamoto, J. et al., "Pathologic support for limited hepatectomy in the treatment of liver metastases from colorectal cancer," Annals of Surgery, vol. 221, No. 1, pp. 74-78, 1995.

Zhang, Z., "Iterative point matching for registration of free-form curves and surfaces," International Journal of Computer Vision, vol. 13, No. 2, pp. 119-152, 1994.

\* cited by examiner

US 8,781,186 B2

SYSTEM AND METHOD FOR ABDOMINAL SURFACE MATCHING USING PSEUDO-FEATURES

This application is a continuation application of PCT International Application PCT/US2011/00786, entitled "System and Method for Abdominal Surface Matching Using Pseudo-Features," filed May 4, 2011, by Logan W. Clements, James D. Stefansic, Prashanth Dumpuri, and Senhu Li, which claims benefit of and priority to U.S. Provisional Application No. 61/331,252, filed May 4, 2010, by Logan W. Clements, et al., and is entitled to those filing dates in whole or in part for priority. The specification, figures and complete disclosures of the above-identified U.S. Provisional Application No. 61/331,252 and PCT International Application PCT/US2011/00786 are incorporated herein by specific reference for all purposes.

This invention was made with the partial support of the United States government under NIH SBIR Grant Contract No. CA119502. The Government may have certain rights in this invention.

FIELD OF INVENTION

This invention relates generally to a system and related methods for abdominal surface matching for image-guidance during percutaneous surgical procedures.

BACKGROUND OF THE INVENTION

Image-guided therapy (IGT), which is also often referred to as image-guided intervention (IGI), has gained widespread attention and clinical acceptance for use in localizing tumors in abdominal organs. Procedures that utilize IGT include, but are not limited to, tumor biopsy and ablation.

IGT essentially describes the interactive use of medical images during a percutaneous procedure, and is often referred to as a "global positioning system" (GPS) for interventional radiology. For example, in an automobile GPS, the current position of a vehicle is accurately localized or "registered" onto an electronic roadmap located on the dashboard. As the automobile moves, its position is updated on this roadmap. The driver can use the GPS as a guide to see where their vehicle is, where it has been and where it is headed, and can follow a planned route to a selected destination. IGT allows the physician to accomplish the same thing with their tracked medical instruments on the 3-D "roadmap" of highly detailed tomographic medical images of the patient that are ideally acquired and studied well before the interventional procedure. The key step in an IGT procedure is the accurate registration between real "patient" space and medical image space.

In an ideal IGT procedure, a 3D map or plan is created from the preoperative diagnostic images, possibly days before the actual procedure and in consultation with a variety of physicians in different disciplines. On the day of the percutaneous procedure, the position of the patient and the medical instruments are accurately localized or "registered" onto these pre-operative images in the interventional suite. As the physician moves the instrument, the precise location of its tip is updated on the 3-D images. The physician can then quickly follow a planned path to a selected destination (for example, a tumor or other lesion of interest). The exact location of the instrument is confirmed with a form of real-time imaging, including, but not limited to, intraoperative computerized tomography (CT), 2-D fluoroscopy, or ultrasonic (US) imaging.

U.S. Pat. No. 7,853,307, "Methods, Apparatuses, And Systems Useful In Conducting Image Guided Interventions," which is incorporated herein in its entirety by specific reference for all purposes, discloses a method to register the pre-operative images to patient space using non-tissue reference markers/skin fiducial markers. This invention uses radio opaque fiducial markers (also known as skin fiducial markers) attached to the patient's abdomen, and a full CT scan of the patient's abdomen immediately before the procedure (also known as intra-procedural images), and performs a point-based registration to achieve correspondence between the fiducial markers' location on the abdomen and its corresponding position in the intra-procedural CT images. Similarly, U.S. Pat. No. 6,785,571, "Device and Method for Registering A Position Sensor In An Anatomical Body," which is incorporated herein in its entirety by specific reference for all purposes, discloses a method to register pre-operative images to patient space using a tracked instruments inserted into the patient's body.

Both these prior arts suffers from the disadvantage that the highly detailed diagnostic images cannot be easily used during the interventional procedure. This means that the physicians do not have access to detailed visualizations of lesions and vasculature, and also do not have the time to create an ideal procedure plan. The existing technology also requires that the patients be scanned at least twice (once for pre-procedural diagnostic images and a second time for the intra-procedural images), which increases their exposure to X-ray radiations. Therefore, it would be ideal to use the high quality diagnostic CT or MR medical images directly for percutaneous guidance by performing a registration using those images. Point-based registration techniques discussed in the prior art are not accurate and inaccurate registrations compromise the accuracy of guidance during interventional procedures.

U.S. Patent App. No. 60/859,439, "Apparatus And Methods For Compensating For Organ Deformation, Registration Of Internal Structures To Images, And Applications Of The Same," which is incorporated herein in its entirety by specific reference for all purposes, details a method to perform registrations using pre-operative diagnostic images. The registration method disclosed in the patent uses surfaces generated from pre-operative diagnostic images and surfaces obtained during surgical or interventional procedures and "salient anatomical features" (anatomical regions that can be easily identified on both the surfaces) and performs a rigid surface-based registration to align the surfaces obtained during surgical or interventional procedures to the pre-operative surfaces. However, the method relies on the assumption that "salient anatomical features" can be easily identified on both sets of surfaces. Further, "salient anatomical features" cannot be obtained during percutaneous procedures. Therefore, there is a need to perform registration using something other than skin markers and salient anatomical features.

Surface registration using salient anatomical features in image-guided surgery is described more fully in Clements, et al, "Robust surface registration using salient anatomical features in image-guided liver surgery," Medical Imaging 2006: Visualization, Image-guided Procedures, and Display: Proc. of the SPIE (2006), and Clements, et al, "Robust surface registration using salient anatomical features for image-guided liver surgery: Algorithm and validation," Medical Physics, Vol. 35, No. 6, pp. 2528-2540 (2008); copies of the above are appended to U.S. Provisional Application No. 61/331,252, all of which are incorporated herein in their entireties by specific reference for all purposes.

SUMMARY OF INVENTION

In various embodiments, the present invention comprises a system and method for using the contrasted pre-procedural images for interventional guidance. Since the prior art uses intra-procedural images, physicians do not have sufficient time to generate 3D visualizations, nor do they have the time to generate detailed procedural plans. In contrast, the present invention uses 3D visualizations of the vasculature, tumor(s), and organs for enhanced guidance information. The present invention further facilitates extensive pre-procedural planning, thereby significantly reducing procedural times. Since this invention uses pre-procedural images instead of intra-procedural images, it also minimizes the patient exposure to radiation. It is also efficient from the perspective of workflow for incorporation into fluoroscopy suites.

In one embodiment of the present invention, pseudo-features and surfaces are used for registration and to establish the relationship needed for guidance. Pseudo-features include defined features identified on the external surface of the patient, and can be obtained using non-contact imaging devices (such as laser range scanning) or contact-based imaging devices (such as handheld ultrasound probes or optically tracked pen probes). Corresponding pseudo-features are marked on the external pre-operative surface obtained from the patient's pre-operative diagnostic images. A registration algorithm combines the pseudo-features with the external surfaces.

In another embodiment, the present invention also uses organ surfaces in addition to the pseudo-features for registration. In one exemplary embodiment, organ surfaces, such as the surface of the liver, obtained from pre-operative diagnostic images, and the intra-operative surface description of the liver, obtained using intra-operative imaging devices such as intra-operative ultrasound or intra-operative CT, are used. These organ surfaces are used to either refine the registration obtained using external surfaces and pseudo-features, or are used as the primary surfaces for registration.

Other exemplary embodiments of the registration include, but are not limited to, an image-based registration using pre-operative diagnostic images and intra-procedural images when obtained.

DETAILED DESCRIPTION OF EXEMPLARY EMBODIMENTS

In one exemplary embodiment, the invention is intended to provide a framework for registering intra-procedural surface images of the abdomen with surfaces extracted from pre-procedural image data (e.g., magnetic resonance imaging (MRI) or computed tomography (CT) volumes) for the purposes of providing image-guidance during percutaneous surgical procedures. Registration is a method of determining the mathematical relationship between two coordinate spaces and is a critical component in image-guided surgery (IGS) devices. The goal of IGS is to allow the clinician to interactively use high resolution, high contrast pre-procedural tomographic image data within the intervention via overlay display of tracked surgical instrumentation.

Intra-procedural surface images of the abdomen can be acquired using laser range scanning (LRS) technology, manually with an optically tracked stylus, or via any other imaging modality that can be used for abdominal surface extraction (e.g., ultrasound, CT, or MRI images acquired during the procedure). The registration process is then used within an image-guidance system to provide the mathematical mapping required to interactively use the pre-procedural image data for guidance within the intervention.

Figure 1:
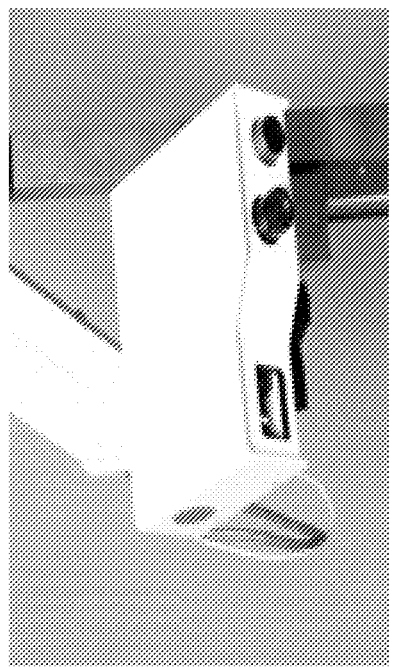
FIG. 1 shows examples of hardware used for purposes of abdominal surface acquisition.
Figure 1:
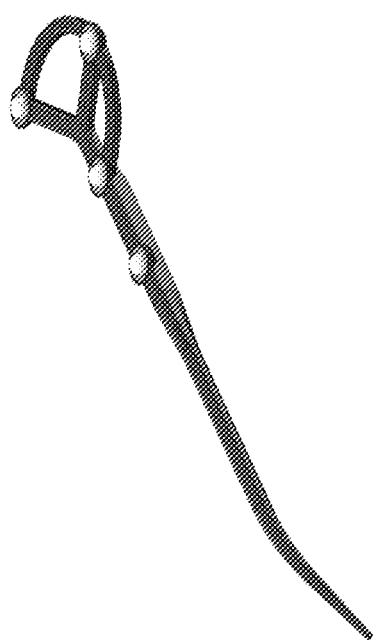

The primary hardware components used in exemplary embodiments of the present invention include those which pertain specifically to the methods of surface and pseudo-feature acquisition during the percutaneous procedure. Examples of such hardware, including an optically tracked probe 2 (left) and a laser range scanner 4 (right), are shown in FIG. 1. Optically tracked probes designed for use with off-the-shelf tracking equipment (such as that provided by Northern Digital, Inc., Waterloo, Ontario) can be used for manual surface acquisition and pseudo-feature delineation. Laser range scanning (LRS) technology can be use to generate high resolution surface scan data in a non-contact fashion. While both technologies are equally useful as exemplary embodiments, other methods of abdominal surface acquisition can be used, including, but not limited to, intraoperative US, CT, or MR.

Figure 2:
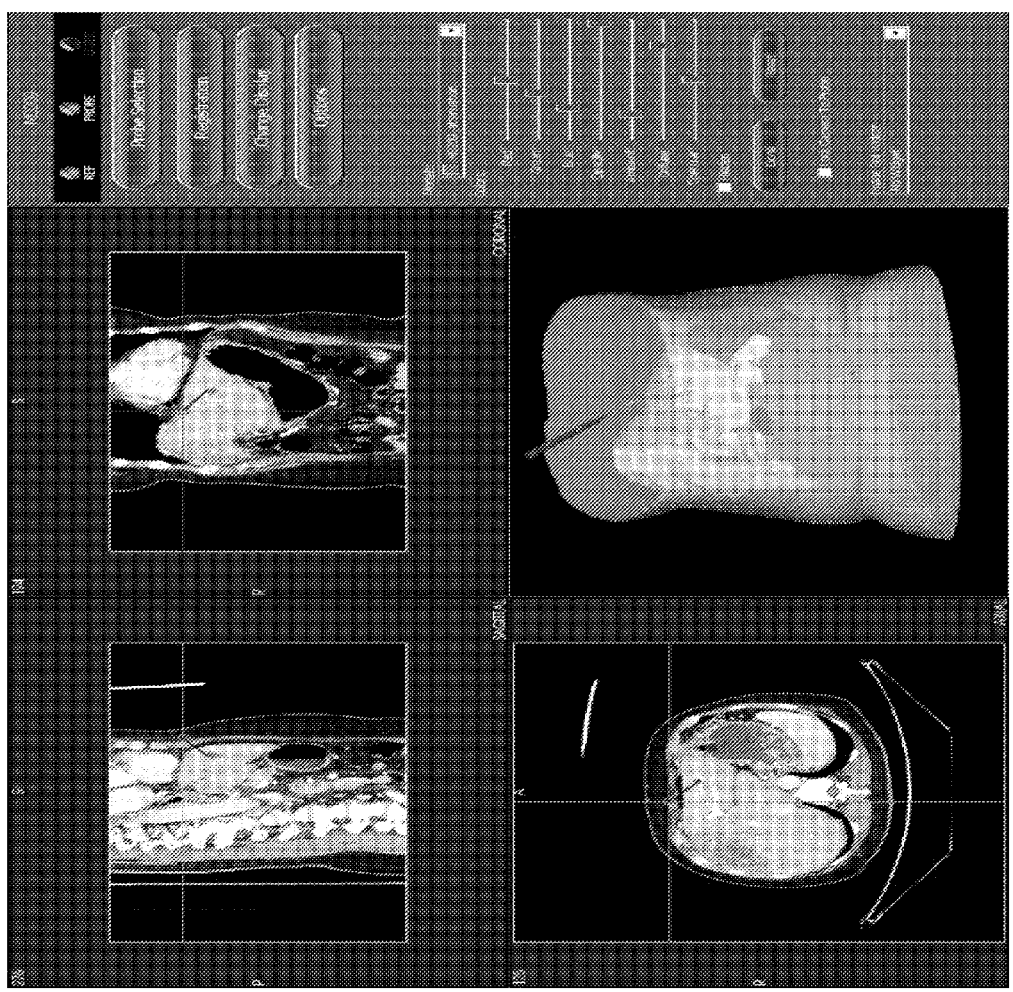
FIG. 2 shows an example of a navigation software program interface for mapping the location of tracked percutaneous ablation instrumentation onto pre-procedural tomographic image data.

In addition to hardware that is capable of performing surface data acquisition during percutaneous procedures, an image guidance device using the methods and system of an embodiment of the present invention may provide guidance information via a software interface. FIG. 2 shows an example of a navigation software interface using an embodiment of the present invention to map the location of tracked percutaneous ablation instrumentation onto the pre-procedural tomographic data. In one specific example, an exemplary embodiment of the invention is used to compute the mathematical transformation that allows for the display of the location of tracked instrumentation on the pre-procedural tomographic image data (shown as the crosshair 6 in FIG. 2). The crosshair 6 location indicates the tracked tip position, while the line 8 (blue, in one embodiment) indicates the trajectory of the instrument. More sophisticated visualizations can be provided wherein the trajectory of the device can be displayed, and the trajectory and device locations can be displayed relative to targets planned prior to surgery. It should be noted that this ability is a differentiating factor between exemplary embodiments of the invention and the prior art. In particular, pre-procedural image data is used for guidance, which allows for pre-procedural planning and 3-D model generation. Guidance visualization such as that shown in the bottom right quadrant of FIG. 2 is not currently possible with the prior art.

In one exemplary embodiment, the method of registration of the present invention comprises the following steps.

1. Extraction of Abdominal Surface and Delineation of Pseudo-Features from the Pre-Procedural Image Data.

First, the abdominal surface is extracted from the preoperative image data. In one embodiment, the abdominal surface extraction method is a semi-automated process that is initialized via input of a seed point within the parenchyma of an abdominal organ. From this seed point, the difference between tissue and air regions can be determined and the abdomen can be extracted. The abdomen surface is then tessellated from the segmented abdomen image in a manner similar to the methods described for liver surface generation in the prior art. In another embodiment, the abdominal surface is generated automatically.

Figure 3:
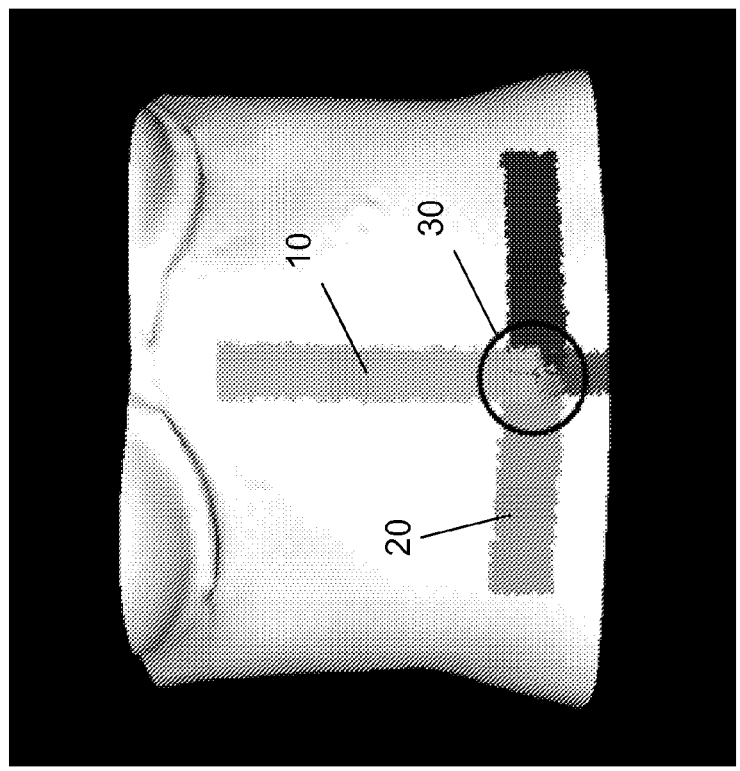
FIG. 3 shows the process of delineation of pseudo-features from the pre-procedural image data.
Figure 3:
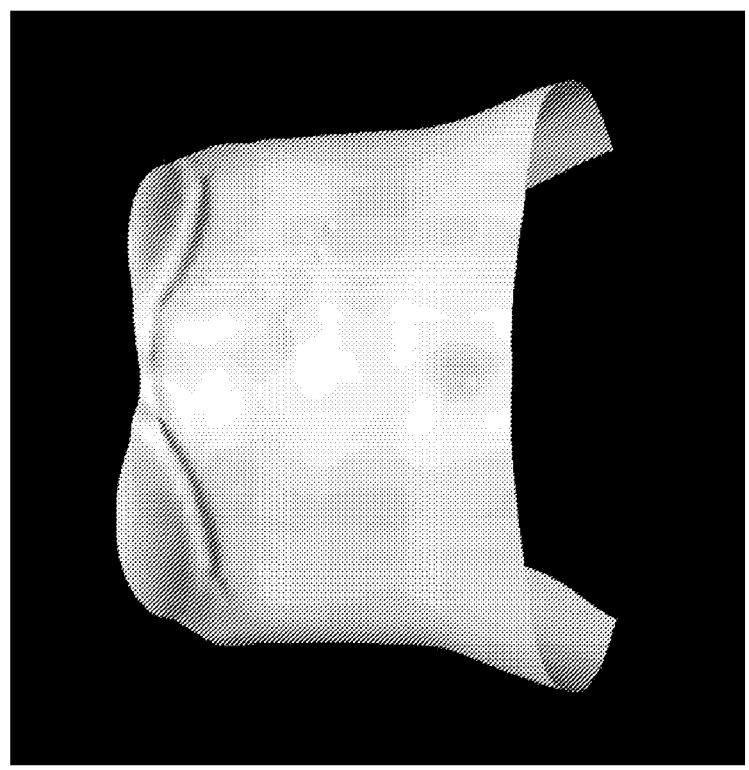

Given the tessellated abdominal surface, a set of pseudo-features are then manually marked on the abdominal surface for use in the registration process. As opposed to the "salient anatomical features" described in the prior art, pseudo-features are regions that can be identified on the abdomen of the patient during the procedure that do not directly correspond with specific anatomical landmarks on the abdomen itself and are not associated with internal organ anatomical regions. "Pseudo-feature" regions are used to initially align the surface data during the registration process. An example of potential pseudo-feature regions, as shown in FIG. 3, involve a strip of feature points 10, 20 marked in the superoinferior direction along the patient's midline and across the patient's abdomen normal to the vertical line intersecting at the navel. This allows the generation of four separate features corresponding with the superior, inferior, left, and right directions.

Additionally, a fifth feature 30 is generated representing the intersection of the four feature regions. Delineating the region of intersection is performed by first finding the overlapping points. After finding the overlapping points within the four regions, the method computes the mean position in the set of overlapping points and then collects all points within a specified radius of the mean overlapping point. Registration accuracy using these five feature regions is appropriate for use in IGS systems. In one exemplary embodiment, registration trials were performed using abdominal surfaces extracted from venous and arterial phase CT sets, with errors determined via manual selection of three vessel bifurcation targets in the image sets. Mean surface residual error was 0.77 mm (2.7 mm maximum), while subsurface target error was 3.3 mm (3.6 mm maximum).

2. Acquisition of Intra-Procedural Surface and Features.

Figure 4:
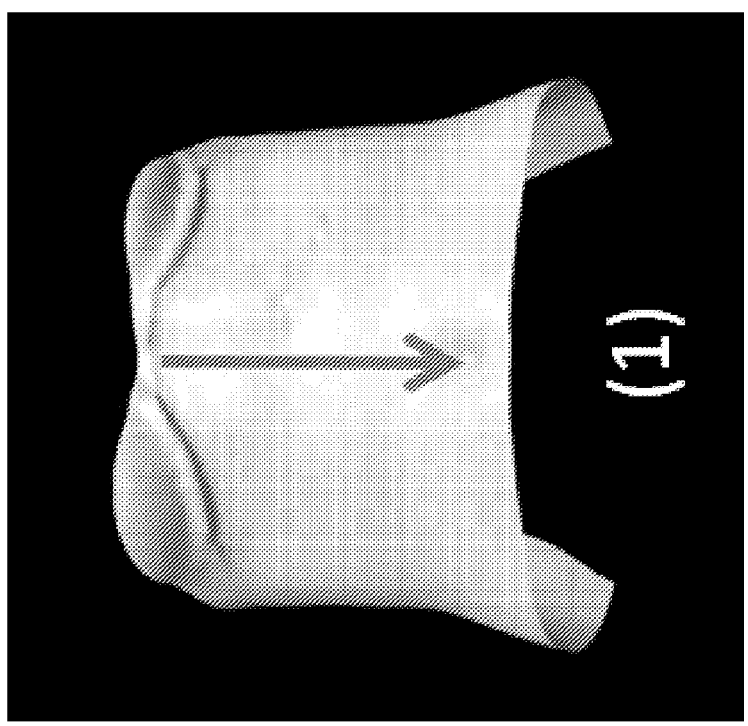
FIG. 4 shows the process of surface registration after delineation of pseudo-feature regions.
Figure 4:
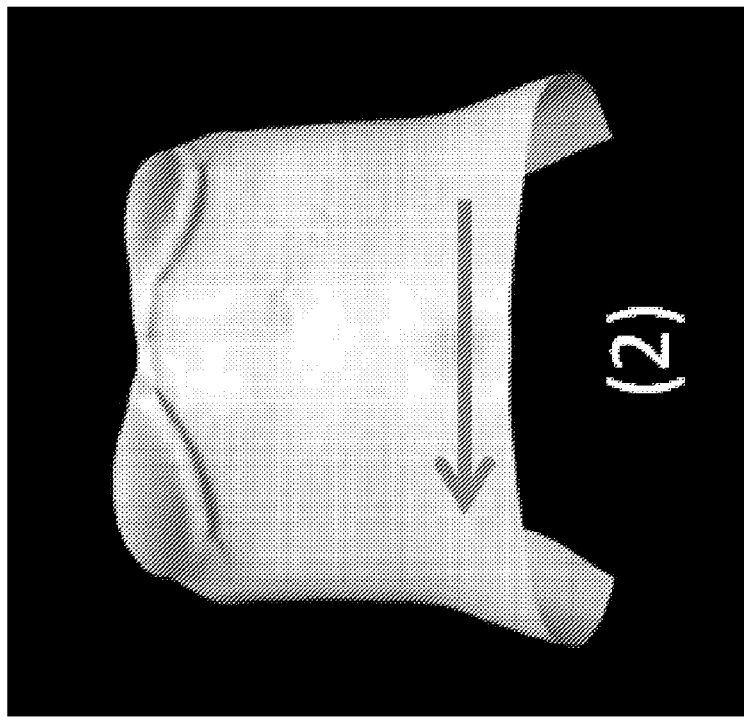

The intra-procedural protocol involves first acquiring a surface image of the patient's abdomen using an LRS device, optically tracked stylus, or any other imaging modality from which the abdominal surface can be extracted. Once the abdomen surface image has been acquired, as shown in FIG. 4, the feature acquisition protocol highlighted is performed. An optically tracked stylus, or similar device, is used by the physician to digitize a contour in the superoinferior direction along the patient midline. Second, a contour is digitized normal to the midline contour from patient left to patient right intersecting the first contour at the navel. As shown in FIG. 3, five separate features are then generated and used in the registration process. Given the a priori information about order of contour acquisitions, the five features can be automatically generated from the two swabbed contours.

3. Calculation of Registration Transform.

Upon the generation of the models and delineation of pseudo-feature regions described above, the surface registration is performed. Surface registration methods can be those described in the prior art.

There are numerous advantages to the present invention over the prior art. The prior art proposes the use of anatomical features for the registration of surface data acquired of internal organ surfaces. However, in the method of the present invention, the feature regions used are "pseudo-features" and do not fall within the definition of "salient anatomical features," which refer to formally defined anatomical landmarks. Additionally, the invention generates registrations for use in IGS technology for percutaneous procedures, while the prior art generates registrations on a specific organ of interest on which surgery will be performed. In other words, the abdominal surface registration generated by the invention can be used for percutaneous interventions on any abdominal organ (e.g., kidney, liver, etc.), while the prior art registration could be performed on the liver, for example, and the guidance information would not be accurate over the kidneys of the patient.

While percutaneous applications are known in the prior art, the present invention is significantly different. The prior art percutaneous systems use point-based methods to perform the registration; in contrast, the present invention is a method for surface-based registration. The point-based registration is performed using skin affixed fiducial markers. Generally speaking, the registration protocol for the alternate embodiments involves the placement of skin affixed markers that can be tracked in the interventional suite. A full CT tomographic image set is then obtained in which the locations of the skin affixed markers can be identified and used for registration.

The distinction between using skin affixed fiducial markers for registration and the surface based method of the invention has a number of direct implications. First, since it is not feasible to use skin affixed markers during the acquisition of the contrasted, pre-procedural diagnostic tomographic image sets, the use of the currently available systems requires a fiducial marker configuration to be affixed to the patient's abdomen immediately prior to the performance of the procedure. Once the fiducial marker setup has been attached to the patient, a full CT scan of the patient's abdomen is performed. While this full CT scan is routinely performed in CT-guided percutaneous procedures, it is not uncommon for this data set to be acquired without contrast agent, which can impair visualization of the lesion as well as vasculature. The present invention allows the initial registration for guidance to be performed without the use of the CT scan that is acquired immediately prior to the procedure since the fiducial markers are not required. This facilitates an even greater minimization of radiation dose than provided by the current systems.

Further, by using the contrasted, pre-procedural image data for interventional guidance, the present invention can utilize extensive 3-D visualizations of the vasculature, tumor(s), and organs for enhanced guidance information. Since the current technology cannot use the pre-procedural CT data for guidance (due to the fiducial marker constraints), sufficient time does not exist to generate the 3-D visualizations for use during the procedure.

Additionally, by circumventing the need to acquire a set of CT images immediately prior to performing image-guidance, the present invention is much more efficient from the perspective of workflow for incorporation into fluoroscopy suites. Fluoroscopy allows the acquisition of 2-D projection images that are real-time and is frequently used for catheter placement procedures that would benefit greatly from 3-D image guidance. As discussed above, the requirement of skin-affixed fiducials in the alternate embodiments necessarily requires a CT scan to be acquired immediately before the use of the guidance system. This required scan imposes a less efficient workflow than would be necessary for a device using the invention.

Finally, more extensive procedural planning can be incorporated with use of the present invention, given the ability to use the pre-procedural image data. Planning the needle entry point on the abdomen and required needle trajectories is of significant benefit in reducing procedure times and patient exposure to radiation.

In order to demonstrate the application and validity of the methods of the present invention, a set of simulation registration trials were performed. Abdominal surface and organ models were generated from a sample set of CT images, shown in FIG. 5. The visualization of FIG. 5 includes models of the liver, hepatic and portal veins, pancreas, kidneys, and spleen, as well as the locations of the anatomical fiducials used to compute the target errors in the simulation experiments. The anatomical targets points used in the experiments are as follows: (1) right hepatic vein insertion, (2) portal vein bifurcation, (3) gallbladder fossa, (4) right renal vein insertion, (5) left renal vein insertion, (6) splenic vein insertion, and (7) superior mesenteric artery near the pancreas.

Once the abdominal surface and organ surface models were generated, the pseudo-features were delineated on the abdominal surface. Simulated LRS-based and probe-based abdominal surface acquisitions were generated using a portion of the full abdominal surface generated from the CT image set and a set of perturbation trials were performed to ascertain the registration accuracies of the device using the two potential embodiments.

The simulated LRS-based surface acquisitions included surfaces comprised of 12,000 and 5,000 total surface and pseudo-feature points. As manually acquired surfaces will be sparser compared with LRS data, the simulated probe-based surfaces were comprised of 5,000 and 3,000 points. The overall extent of the full CT abdominal surface used in generating the simulated surfaces was a reasonable estimate of the extent of the abdomen that can be acquired during a percutaneous intervention.

In order to simulate localization error in the surface acquisition process, each of the surface points were perturbed by a random displacement vector. Registration trials (N=200) were performed over three different maximum vector magnitudes. The maximum vector magnitudes were selected to be 1 mm and 5 mm for the simulated LRS-based acquisitions while vector magnitudes of 10 mm and 20 mm were selected for the simulated probe-based surface acquisitions. Higher magnitudes were selected for the simulated probe-based surfaces due to the fact that there is a higher propensity for manual errors in surface acquisition using this technique (e.g., lifting of the probe off the abdomen surface slightly during acquisition). It should be noted that vector magnitudes of 5 mm and 20 mm represent the very high end of the conceivable range of errors associated with surface acquisitions using the two exemplary embodiments. The random vectors and magnitudes were generated using a uniformly distributed random number generator.

In addition to the displacement vector perturbations, the initial alignment of the surfaces was also perturbed for each registration trial. The random transformations were computed by generating a set of six random parameters (i.e., three translation and three rotation). A uniformly distributed random number generator was used to supply the rotation parameters ($\theta_x, \theta_y, \theta_z$) and translation parameters ($t_x, t_y, t_z$) for the perturbation transformation matrices. The rotation parameters were generated on the interval [−180°, 180°] ($\mu$=−0.7±106.1) and the translation parameters were generated on the interval [−200 mm, 200 mm] ($\mu$=−3.4±119.3). The registrations were then computed using the surface registration algorithm described by the prior art (i.e., in the Clements, et al, references identified previously).

The results for the simulated LRS-based abdominal registrations are summarized in Table 1 below. The results of the perturbation registrations are reported both in terms of the surface root mean square (RMS) residual (i.e., the RMS of the closest point distances between the source and target surfaces) and the sub-surface landmark target registration error (i.e., RMS distance between the internal anatomical target positions after registration). The distribution of the seven sub-surface anatomical targets used in the registration trials are shown in FIG. 3. The targets selected include various vessel targets in a variety of internal abdominal organs that could be targeted for percutaneous intervention.

TABLE 1

| Target | 12,000 Point Sampling | | 5000 Point Sampling | |
|---|---|---|---|---|
| | 1 mm Perturbation | 5 mm Perturbation | 1 mm Perturbation | 5 mm Perturbation |
| (1) Right Hepatic Vein Insertion | 0.82 ± 0.82 (1.9) | 0.09 ± 0.24 (3.4) | 0.88 ± 0.85 (1.9) | 0.15 ± 0.05 (0.31) |
| (2) Portal Vein Bifurcation | 0.68 ± 0.67 (1.4) | 0.07 ± 0.16 (2.2) | 0.70 ± 0.66 (1.5) | 0.10 ± 0.04 (0.27) |
| (3) Gallbladder Fossa | 0.71 ± 0.70 (1.5) | 0.07 ± 0.14 (2.0) | 0.71 ± 0.68 (1.5) | 0.10 ± 0.04 (0.28) |
| (4) Right Renal Vein Insertion | 0.54 ± 0.55 (1.3) | 0.06 ± 0.09 (1.3) | 0.51 ± 0.49 (1.4) | 0.10 ± 0.05 (0.33) |
| (5) Left Renal Vein Insertion | 0.34 ± 0.36 (0.93) | 0.07 ± 0.14 (2.0) | 0.40 ± 0.40 (1.1) | 0.10 ± 0.05 (0.27) |
| (6) Splenic Vein Insertion | 0.50 ± 0.57 (1.4) | 0.08 ± 0.23 (3.2) | 0.62 ± 0.64 (1.5) | 0.11 ± 0.06 (0.31) |
| (7) Superior Mesenteric Artery | 0.39 ± 0.39 (0.86) | 0.06 ± 0.13 (1.8) | 0.41 ± 0.39 (0.89) | 0.09 ± 0.05 (0.22) |
| MEAN | 0.57 ± 0.56 (1.2) | 0.07 ± 0.16 (2.3) | 0.60 ± 0.57 (1.3) | 0.10 ± 0.04 (0.26) |

Table 1 summarizes the registration results in terms of sub-surface target errors target errors [stated in mm units−mean±standard deviation (maximum)] using the simulated LRS-based surface acquisitions. The surfaces used were comprised of a total of approximately 12,000 and 5,000 surface and pseudo-feature points and 200 perturbation registrations were performed for each combination of surface sampling and noise displacement magnitude. For reference, the closest point distances over the trials using the 12,000 point surface were 0.72±0.16 mm (0.93 mm maximum) and 1.84±0.02 mm (2.04 mm maximum) for the 1 mm and 5 mm maximum displacement magnitudes. The closest point distance errors using the 5,000 point surface were 0.73±0.17 mm (0.96 mm maximum) and 1.84±0.02 mm (1.88 mm maximum) for the 1 mm and 5 mm maximum displacement magnitudes.

Figure 6:
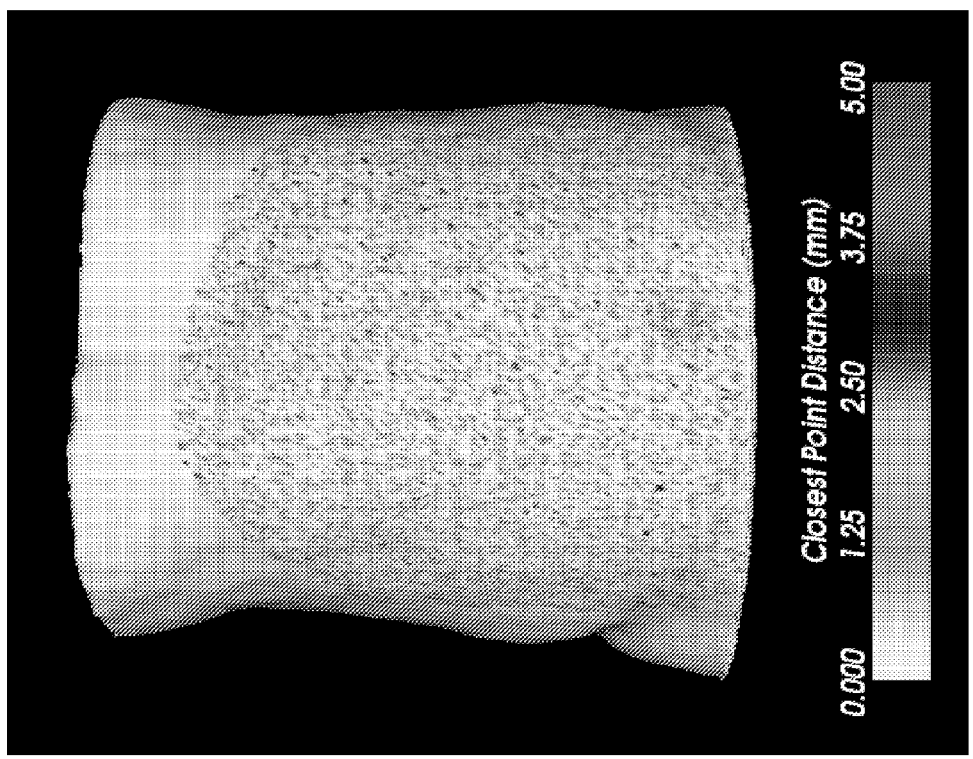
FIG. 6 shows an example of a visualization of a sample abdominal registration result and texture mapping of the closest point distance measurements between the two surfaces.
Figure 6:
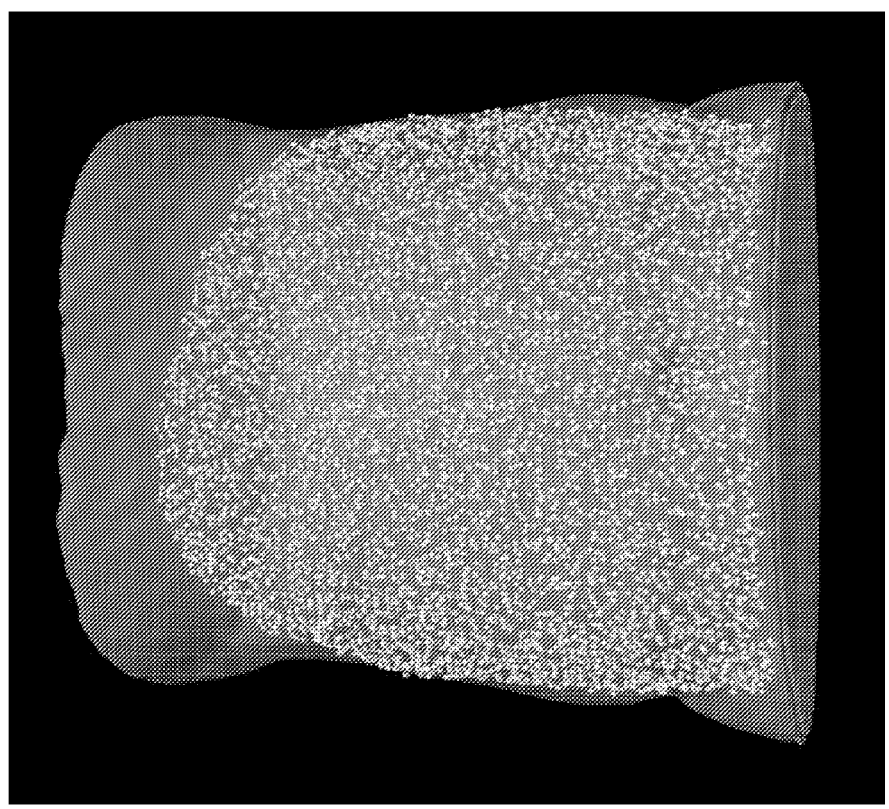
Figure 7:
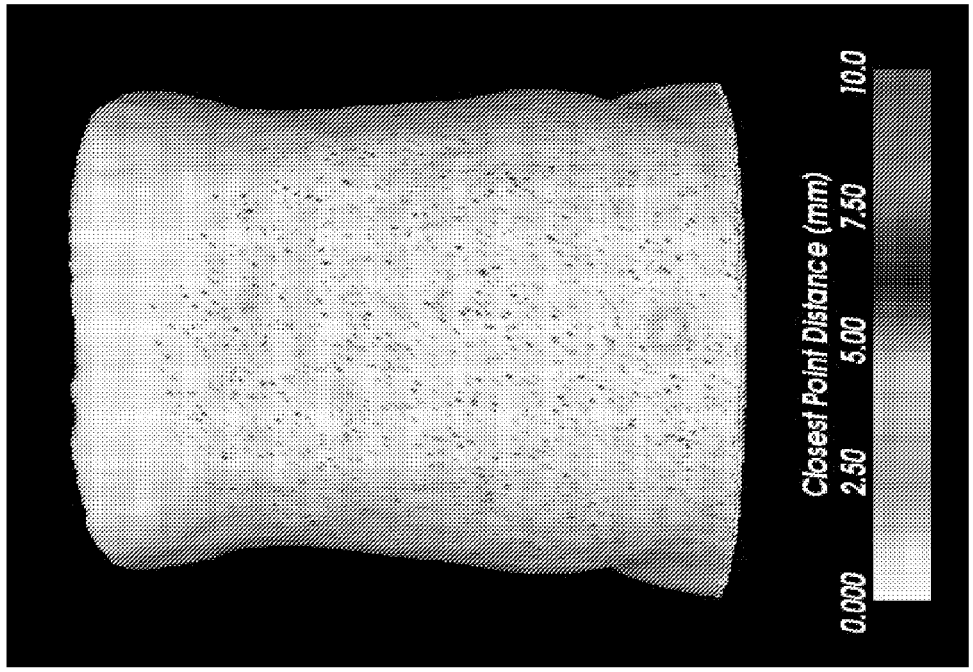
FIG. 7 shows another example of a visualization of a sample abdominal registration result and texture mapping of the closest point distance measurements between the two surfaces.
Figure 7:
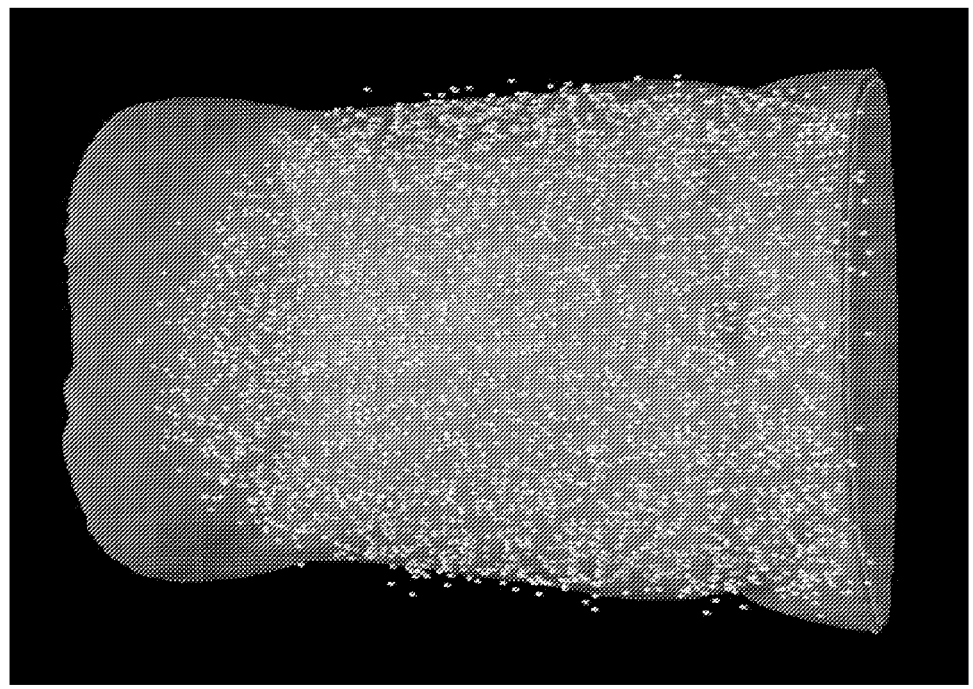

An example registration result from one of the registration trials is shown in FIG. 6. FIG. 6 is a visualization of a sample abdominal registration result (left) and texture mapping of the closest point distance measurements between the two surfaces (right) computed for the simulated LRS-based abdominal surface acquisition including approximately 12,000 total surface and pseudo-feature points and a maximum noise magnitude of 5 mm. For reference, the mean closest point distance between the surfaces was found to be 1.16 mm (3.57 mm maximum).

It should be noted that over all of the registration trials (N=800) and for all anatomical targets, the mean target registration error (TRE) was less than 1 mm. Further, there seems to be little correlation between the degree of surface error perturbation and the overall target accuracy of the exemplary embodiment. The overall surface errors do, however, increase with the maximum magnitude of the random perturbation vector representing noise in the surface acquisition. However, this test demonstrates that an LRS-based embodiment of the present invention provides sufficient guidance accuracy for use in percutaneous interventions.

The results for the simulated probe-based surface registrations are summarized in Table 2 below.

abdominal registration result (left) and texture mapping of the closest point distance measurements between the two surfaces (right) computed for the simulated probe-based abdominal surface acquisition including approximately 3,000 total surface and pseudo-feature points and a maximum noise magnitude of 20 mm. For reference, the mean closest point distance between the surfaces was found to be 2.91 mm (14.95 mm maximum).

It should be noted that while extremely large maximum perturbation vector magnitudes were used to simulate noise in the manual abdominal surface collection process, the average target errors were found to be less than 1 mm for all trials except for the abdominal surface sampled at 3,000 points and subject to a maximum noise vector magnitude of 2 cm. Even given the use of extreme noise perturbation magnitudes, the maximum errors over all trials (N=800) and over all anatomical targets were found to be less than 4 mm. The TRE errors shown in Table 2 indicate that the exemplary embodiment of probe-based, manual abdominal surface and pseudo-feature acquisitions for registration in percutaneous image guidance provides information of sufficient accuracy to be clinically useful.

In addition to simply using the abdominal surface for the purposes of registration for percutaneous image guidance, in another exemplary embodiment additional surface data acquired of the internal organs is used to facilitate registration. Such surface data can be acquired through a variety of

TABLE 2

| Targets | 5,000 Point Sampling | | 3,000 Point Sampling | |
|---|---|---|---|---|
| | 10 mm Perturbation | 20 mm Perturbation | 10 mm Perturbation | 20 mm Perturbation |
| (1) Right Hepatic Vein Insertion | 0.36 ± 0.33 (1.7) | 0.93 ± 0.53 (3.1) | 0.53 ± 0.41 (1.9) | 1.2 ± 0.57 (3.1) |
| (2) Portal Vein Bifurcation | 0.33 ± 0.34 (1.8) | 0.96 ± 0.57 (3.4) | 0.49 ± 0.42 (2.2) | 1.1 ± 0.62 (3.3) |
| (3) Gallbladder Fossa | 0.34 ± 0.36 (1.9) | 1.0 ± 0.62 (3.6) | 0.51 ± 0.45 (2.4) | 1.2 ± 0.70 (3.6) |
| (4) Right Renal Vein Insertion | 0.29 ± 0.29 (1.6) | 0.83 ± 0.47 (3.0) | 0.44 ± 0.36 (1.7) | 0.99 ± 0.55 (2.9) |
| (5) Left Renal Vein Insertion | 0.30 ± 0.31 (1.8) | 0.80 ± 0.50 (3.2) | 0.42 ± 0.38 (1.9) | 0.97 ± 0.51 (2.9) |
| (6) Splenic Vein Insertion | 0.33 ± 0.32 (1.9) | 0.86 ± 0.50 (3.2) | 0.46 ± 0.39 (1.8) | 1.1 ± 0.54 (2.8) |
| (7) Superior Mesenteric Artery | 0.29 ± 0.33 (1.8) | 0.84 ± 0.52 (3.3) | 0.43 ± 0.39 (2.0) | 0.95 ± 0.54 (2.9) |
| MEAN | 0.32 ± 0.31 (1.7) | 0.90 ± 0.48 (3.2) | 0.47 ± 0.38 (2.0) | 1.1 ± 0.50 (2.8) |

Table 2 summarizes the registration results in terms of sub-surface target errors [stated in mm units–mean±standard deviation (maximum)] for the simulated probe-based surface acquisitions. The surfaces used were comprised of a total of approximately 5,000 and 3,000 surface and pseudo-feature points and 200 perturbation registrations were performed for each combination of surface sampling and noise displacement magnitude. For reference, the closest point distances over the trials using the 5,000 point surface were 3.42±0.04 mm (3.5 mm maximum) and 6.68±0.07 mm (6.8 mm maximum) for the 10 mm and 20 mm maximum displacement magnitudes, respectively. The closest point distances for the trials performed with the 3,000 point surface were over the 3.42±0.04 mm (3.5 mm maximum) and 6.67±0.09 mm (6.9 mm maximum) for the 10 mm and 20 mm maximum displacement magnitudes, respectively.

Figure 5:
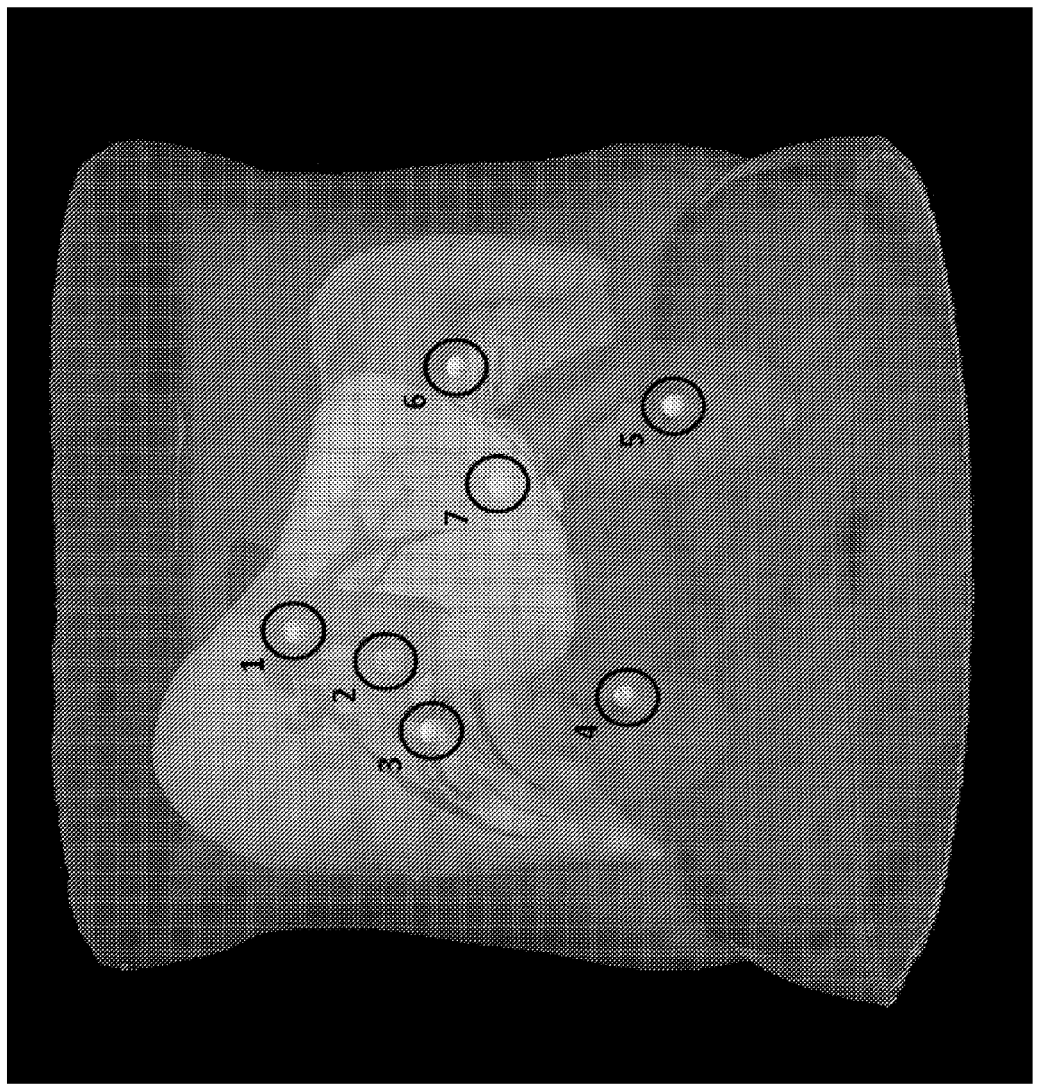
FIG. 5 shows an example of a visualization of the abdominal surface and organ models used in validation trials.

A sample registration result from one of the perturbation trials is provided for visualization in FIG. 5. Shown is the imaging modalities. In one embodiment, the organ surface imaging is derived from ultrasound imaging. Such additional surface data helps to improve the accuracy of the device with respect to the specific internal organ. Further, this particular embodiment is completely novel with respect to the prior art used in percutaneous procedures. All known prior art in the realm of percutaneous image guidance use a fiducial apparatus that is attached to the abdomen of the patient for the purposes of registration, and no surface or other information from imagery of the internal organs is used.

In a further experiment, simulated ultrasound surface data of the liver was generated to be used in addition to the simulated abdominal surface data used in the previous registration trials described above. The surface sampling used in the registration experiment included the 5,000 point abdominal and pseudo-feature surface along with a simulated liver surface derived from ultrasound of 1,000 points. Additionally, the 3,000 point abdominal and pseudo-feature surface was used in conjunction with a 500 point simulated liver surface.

As was performed in the previous experiment, noise in the surface acquisitions was simulated via the addition of a random displacement vector generated for each of simulated surface points. Trials were performed using a maximum displacement vector magnitude of 10 mm. Additionally, the initial alignment between the two surfaces was generated via perturbation with a random transformation matrix as described previously. The surface registration performed then proceeded as described in the prior art (as described in the Clements references identified above).

The results for the simulated abdominal surface and pseudo-feature data used in conjunction with internal organ surface data are summarized in Table 3 below.

TABLE 3

| Target | 5,000 Point Abdomen & 1,000 Point Liver Sampling 10 mm Perturbation | 3,000 Point Abdomen & 500 Point Liver Sampling 10 mm Perturbation |
|---|---|---|
| (1) Right Hepatic Vein Insertion | 0.30 ± 0.32 (1.6) | 0.45 ± 0.41 (1.9) |
| (2) Portal Vein Bifurcation | 0.29 ± 0.35 (1.7) | 0.44 ± 0.46 (2.1) |
| (3) Gallbladder Fossa | 0.29 ± 0.36 (1.7) | 0.46 ± 0.50 (2.3) |
| (4) Right Renal Vein Insertion | 0.28 ± 0.31 (1.6) | 0.41 ± 0.39 (1.9) |
| (5) Left Renal Vein Insertion | 0.30 ± 0.31 (1.6) | 0.43 ± 0.40 (2.1) |
| (6) Splenic Vein Insertion | 0.31 ± 0.30 (1.6) | 0.45 ± 0.41 (2.1) |
| (7) Superior Mesenteric Artery | 0.29 ± 0.34 (1.7) | 0.42 ± 0.44 (2.0) |
| MEAN | 0.29 ± 0.32 (1.6) | 0.44 ± 0.42 (2.0) |

Table 2 summarizes the registration results in terms of sub-surface target errors [stated in mm units–mean±standard deviation (maximum)] using the simulated probe-based surface acquisitions in conjunction with simulated liver surface data derived from ultrasound imaging. The surfaces used were comprised of a total of approximately 5,000 abdominal surface and pseudo-feature points with 1,000 liver surface points and 3,000 abdominal surface and pseudo-feature points with 500 liver surface points. 200 perturbation registrations were performed for each combination of surface sampling and noise displacement magnitude. For reference, the closest point distance over the trials using the 5,000 point abdominal surface and 1,000 point liver surface was 3.42±0.03 mm (3.5 mm maximum). The closest point distance for the trials performed with the 3,000 point abdominal surface and 500 point liver surface was 3.42±0.04 mm (3.5 mm maximum).

Figure 8:
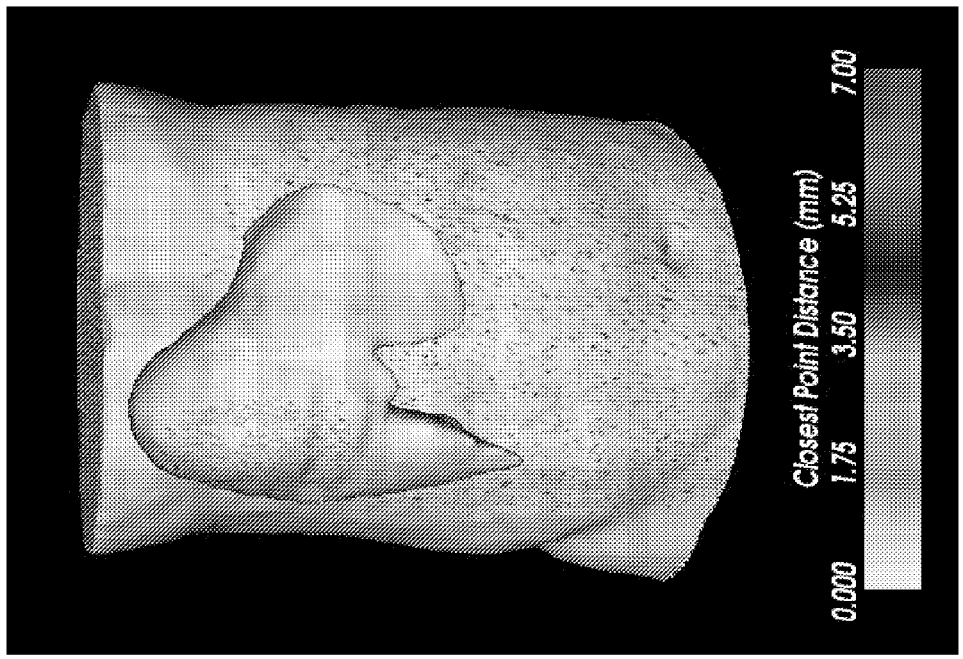
FIG. 8 shows another example of a visualization of a sample abdominal registration result and texture mapping of the closest point distance measurements between the two surfaces.
Figure 8:
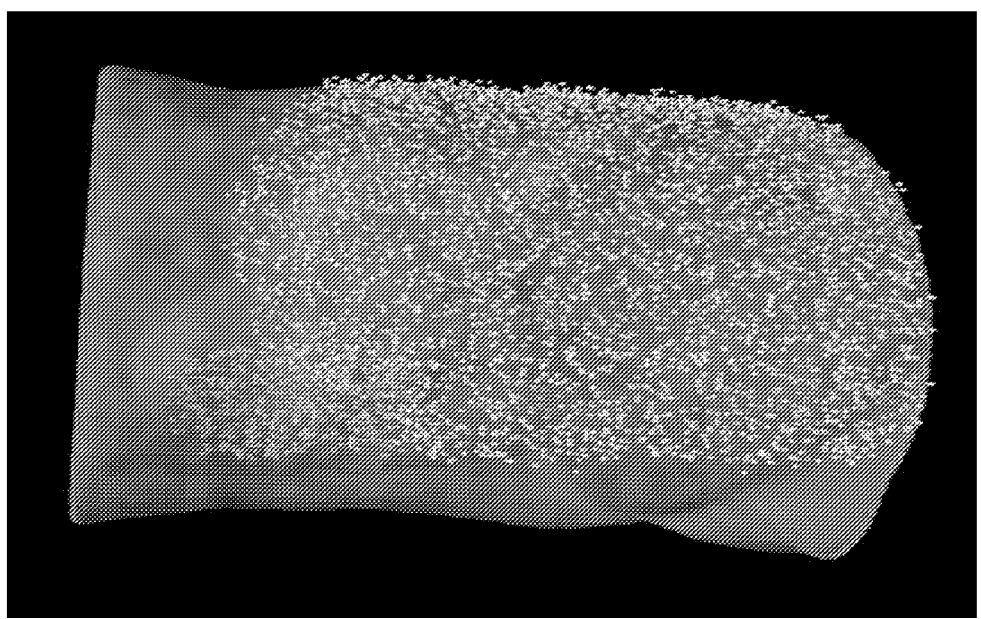

A visualization of a sample registration performed as part of this experiment is shown in FIG. 8. Shown is a sample abdominal registration result (left) and texture mapping of the closest point distance measurements between the two surfaces (right) computed for the simulated probe-based abdominal surface acquisition including the simulated ultrasound surface data of the liver. The simulated surface shown included approximately 5000 total abdominal surface and pseudo-feature points as well as approximately 1000 simulated liver surface points acquired via ultrasound imaging. A maximum noise vector magnitude of 10 mm was used in the visualized registration. For reference, the mean closest point distance between the surfaces was found to be 1.84 mm (6.70 mm maximum).

The results indicate that including the internal organ surface data results in TRE measurements of less than 1 mm on average and that the registration accuracies are similar to those reported in Table 2. Additionally, the maximum TRE measurement over all of the registration trials (N=400) and over all anatomical targets was found to be 2.3 mm. As with the exemplary embodiment using probe-based abdominal and pseudo-feature acquisitions, the data in Table 3 show that including internal organ surfaces also provides suitable registration accuracies for the purposes of percutaneous image guidance.

Additional embodiments include, but are not limited to, the following:

The acquisition of abdominal surface and pseudo-feature data using different imaging and instrumentation.

Examples of embodiments include surface acquisition using optically or magnetically tracked stylus devices for manual use as well as non-contact imaging devices (e.g., laser range scanning) that can be used for automatic acquisition of abdominal surface and surface pseudo-features.

The abdominal surfaces with pseudo-features are then used for the purposes of calculating the mathematical registration transform required for use in image-guidance devices.

Performance of surface matching for percutaneous image guidance using a combination of abdominal surface with pseudo-features and internal organ surface(s) extracted from other imaging modalities.

An exemplary embodiment includes the use of liver surface data extracted from ultrasound (US) images as well as the abdominal surface data acquired with a tracked stylus to perform the registration for percutaneous image guidance.

Refining of abdominal surface matching with pseudo-features with organ surface acquisitions extracted from other imaging modalities.

An exemplary embodiment is for the guidance system to compute the registration between the pre-procedural tomographic image data and the intra-operative abdominal surface with pseudo-features. This initial registration is then be used as an initial pose to compute a refined registration between an internal abdominal organ surface acquired in the operative suite and the organ surface extracted from pre-procedural image data.

Providing percutaneous guidance information on procedural tomographic image sets via image-to-image registration of procedural image data to pre-procedural image data.

Since the percutaneous image guidance device performs registration between the pre-procedural tomographic images, it is possible to extend the percutaneous guidance information to the image data acquired throughout the procedure in "real time" by performing a registration between the "real time" procedural image data and the pre-procedural image data.

Thus, it should be understood that the embodiments and examples described herein have been chosen and described in order to best illustrate the principles of the invention and its practical applications to thereby enable one of ordinary skill in the art to best utilize the invention in various embodiments and with various modifications as are suited for particular uses contemplated. Even though specific embodiments of this invention have been described, they are not to be taken as exhaustive. There are several variations that will be apparent to those skilled in the art.

What is claimed is:

1. A method for performing registration for percutaneous surgical procedures, comprising the steps of:
   generating a computer model of a portion of an outer surface of a patient from pre-procedural image data;
   marking a set of pseudo-features on the generated computer model of the portion of the outer surface;
   acquiring an intra-procedural image of a corresponding portion of the outer surface of the patient;
   generating a set of intra-procedural pseudo-features by digitizing one or more contours on the corresponding portion of the outer surface of the patient; and
   performing an alignment or registration of the model generated from the pre-procedural data with data from the intra-procedural image.

2. The method of claim 1, wherein the portion of the outer surface of a patient comprises the abdomen of the patient.

3. The method of claim 1, wherein the intra-procedural image of the patient surface is acquired through a laser range scanner, or an optically or magnetically tracked stylus or instrument.

4. The method of claim 1, wherein the set of pseudo-features comprise four quadrants formed by an intersection of a series of points in a superoinferior direction along the patient's midline and across the patient's abdomen normal to a vertical line intersecting at the navel.

5. The method of claim 4, further wherein the set of pseudo-features further comprises a feature representing an intersection of the four quadrants.

6. The method of claim 1, wherein the performing the alignment or registration further comprises the use of pre-procedural surface data for one or more internal organs of the patient.

7. The method of claim 1, further comprising: displaying data for facilitating the percutaneous surgical procedure based on said alignment.

8. The method of claim 7, further wherein the display comprises a three-dimensional model of a portion of the patient.

9. The method of claim 8, wherein the three-dimensional model includes the surface of the patient's abdomen, and one or more organs inside the abdomen.

10. A system for collecting and processing physical space data for use while performing an image-guided surgical (IGS) procedure, the system comprising:
    a storage medium for storing a computer model of a portion of an outer surface of a patient based on pre-operative data;
    at least one sensor device for generating inter-operative surface data associated with said outer surface of the patient; and
    a processing element communicatively coupled to said storage medium and said sensor device, said processing element configured to obtain an alignment of the computer model and inter-operative surface data, the alignment being obtained by the generation of corresponding pseudo-features for the computer model and the intra-operative surface data.

11. The system of claim 10, further comprising a display device communicatively coupled to said processing element and configured to display data for facilitating said IGS procedure based on said alignment.

12. The method of claim 11, further wherein the display comprises a three-dimensional model of a portion of the patient's body.

13. The method of claim 12, wherein the three-dimensional model includes the surface of the patient's abdomen, and one or more organs inside the abdomen.

14. The system of claim 10, wherein the IGS procedure is a percutaneous procedure.

15. The system of claim 10, wherein the storage medium stores a computer model of a non-rigid structure of interest in the patient.

16. The system of claim 10, wherein the portion of the outer surface of the patient's body comprises the outer surface of the abdomen of the patient.

17. The system of claim 10, wherein the sensor device comprises a laser range scanner or an optically or magnetically tracked stylus or instrument.

18. A method, comprising:
    generating an intra-procedural image of a portion of an outer surface of a patient from data acquired during a percutaneous surgical procedure, the intra-procedural image including a set of intra-procedural pseudo-features associated with one or more contours on the portion of the outer surface of the patient; and
    aligning the intra-procedural image with a computer model of the portion of the outer surface of the patient generated from pre-procedural image data acquired prior to the percutaneous surgical procedure to form an aligned image, the computer model including a set of pseudo-features corresponding to regions on the portion of the outer surface of the patient.

19. The method of claim 18, wherein the portion of the outer surface of the patient is an outer surface of the abdomen of the patient.

20. The method of the claim 18, wherein the intra-procedural image is acquired through a laser range scanner, or an optically or magnetically tracked stylus or instrument.

21. The method of claim 18, wherein the set of pseudo-features comprise four quadrants formed by an intersection of a series of points in a superoinferior direction along the patient's midline and across the patient's abdomen normal to a vertical line intersecting at the navel.

22. The method of claim 21, wherein the set of pseudo-features comprises a feature representing an intersection of the four quadrants.

23. The method of claim 18, where in the aligned image includes pre-procedural surface data for one or more internal organs of the patient.

24. The method of claim 18, further comprising displaying a three-dimensional model of the aligned image to facilitate the percutaneous surgical procedure.

25. The method of claim 24, wherein the three-dimensional model of the aligned image includes a three-dimensional model of a surface of the abdomen of the patient, and one or more organs inside the abdomen.

* * * * *